(12) United States Patent
Baker et al.

(10) Patent No.: US 10,492,714 B2
(45) Date of Patent: Dec. 3, 2019

(54) OPTICAL GLUCOMETER

(71) Applicant: FURMAN UNIVERSITY, Greenville, SC (US)

(72) Inventors: William M Baker, Easley, SC (US); M Paige Ouzts, Greenwood, SC (US)

(73) Assignee: FURMAN UNIVERSITY, Greenville, SC (US)

( * ) Notice: Subject to any disclaimer, the term of this patent is extended or adjusted under 35 U.S.C. 154(b) by 0 days.

(21) Appl. No.: 16/084,880

(22) PCT Filed: Sep. 20, 2017

(86) PCT No.: PCT/US2017/052467
§ 371 (c)(1),
(2) Date: Sep. 13, 2018

(87) PCT Pub. No.: WO2018/057598
PCT Pub. Date: Mar. 29, 2018

(65) Prior Publication Data
US 2019/0336052 A1    Nov. 7, 2019

Related U.S. Application Data

(60) Provisional application No. 62/397,181, filed on Sep. 20, 2016.

(51) Int. Cl.
| | | |
|---|---|---|
| *A61B 5/1455* | (2006.01) | |
| *A61B 5/145* | (2006.01) | |
| *A61B 5/01* | (2006.01) | |
| *A61B 3/14* | (2006.01) | |
| *G01N 21/35* | (2014.01) | |
| *G01J 3/443* | (2006.01) | |
| *A61B 5/00* | (2006.01) | |

(52) U.S. Cl.
CPC ............ *A61B 5/14532* (2013.01); *A61B 3/14* (2013.01); *A61B 5/015* (2013.01); *A61B 5/1455* (2013.01); *G01N 21/35* (2013.01); *A61B 5/6821* (2013.01); *G01J 3/443* (2013.01)

(58) Field of Classification Search
CPC .............. A61B 5/1455; A61B 5/14551; A61B 5/14532; A61B 5/015; A61B 5/6821
See application file for complete search history.

(56) References Cited

U.S. PATENT DOCUMENTS

| | | | |
|---|---|---|---|
| 5,941,821 A | 8/1999 | Chou | |
| 6,226,089 B1* | 5/2001 | Hakamata | A61B 5/14532 356/432 |
| 9,724,022 B2* | 8/2017 | Li | A61B 5/14532 |
| 2004/0220458 A1 | 11/2004 | Burd et al. | |
| 2005/0010091 A1 | 1/2005 | Woods et al. | |
| 2005/0085701 A1 | 4/2005 | Burd et al. | |
| 2006/0258920 A1* | 11/2006 | Burd | A61B 5/14532 600/319 |

* cited by examiner

*Primary Examiner* — Eric F Winakur
*Assistant Examiner* — Chu Chuan Liu
(74) *Attorney, Agent, or Firm* — Parker Poe Adams & Bernstein, LLP

(57) ABSTRACT

Disclosed herein are devices and methods for detecting blood glucose levels in a subject that involve passively quantifying mid-infrared emissions from the eye of the subject.

28 Claims, 44 Drawing Sheets

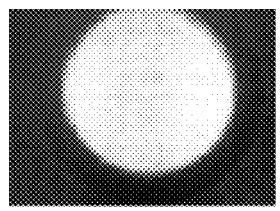 IMAGE OF BLACK BODY REFERENCE
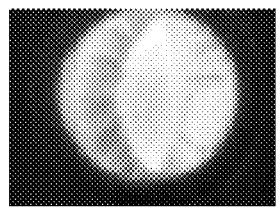 IMAGE OF PATIENT'S EYE
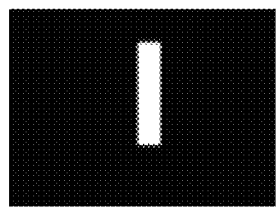 MASK
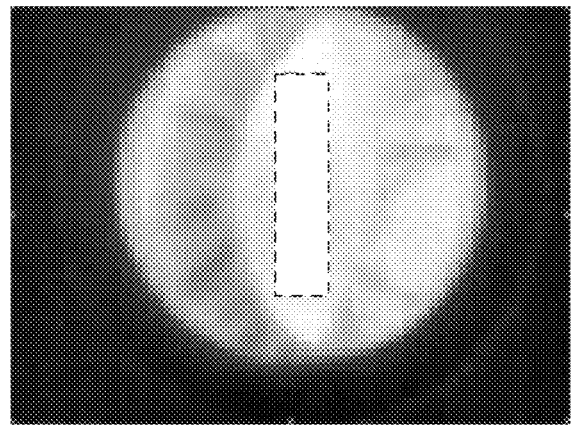 APPLICATION OF MASK TO IMAGE
FIG. 31

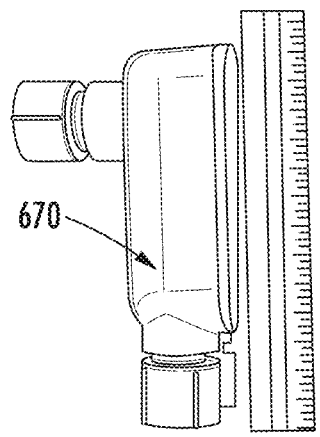
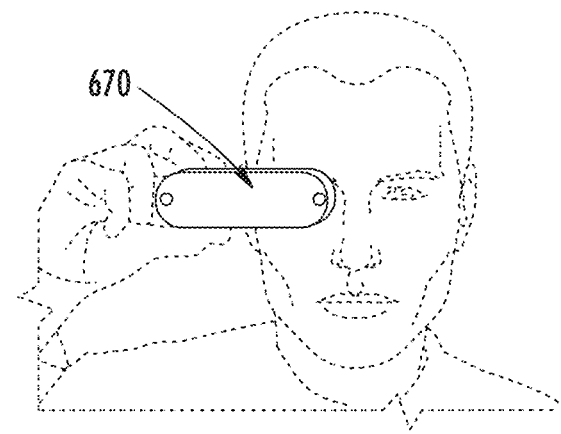
FIG. 36A          FIG. 36B
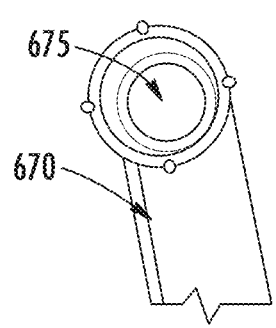
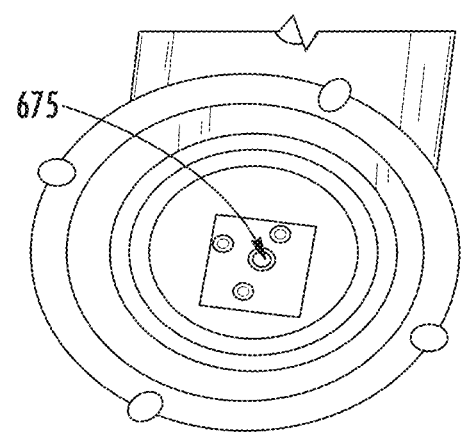
FIG. 36C          FIG. 36D

OPTICAL GLUCOMETER

CROSS-REFERENCE TO RELATED APPLICATIONS

This application claims the benefit of U.S. Provisional Patent Application No. 62/397,181, filed on Sep. 20, 2016, entitled "OPTICAL GLUCOMETER," the disclosure of which is expressly incorporated herein by reference in its entirety.

TECHNICAL FIELD

This invention relates to non-invasive optical methods and devices for measuring blood glucose concentrations.

BACKGROUND

Many diabetics are asked to test their blood glucose up to six times or more per day in order to adjust their insulin doses for tighter control of their blood glucose levels. As a result of the discomfort, many of these patients do not test as often as is recommended by their physician, with the consequence of poor blood glucose control. This poor control has been shown to result in increased complications from this disease. Among these complications are blindness, heart disease, kidney disease, ischemic limb disease, and stroke. It would thus be desirable to obtain fast and reliable measurements of blood glucose concentration using easier and less invasive methods.

D-Glucose or Dextrose monohydrate is a simple molecule with the chemical formula of $C_6H_{12}O_6$ yet determining the concentration in blood using optical methods is complex. This molecule has signature vibrational modes in the infrared region of the electromagnetic spectrum. These vibrational bands allow for spectral identification of the molecule. In the region of interest 980-1200 $cm^{-1}$, these spectral peaks are attributed to the C—O stretch in the glucose molecule.

SUMMARY

Disclosed herein are devices and methods for detecting blood glucose levels in a subject that involve passively quantifying mid-infrared emissions from the eye of the subject. In some embodiments, the mid-infrared emissions are quantified at a wavelength of 8 to 11 μm. The devices and methods can then involve comparing the mid-infrared emissions to control values (e.g. control values standardized to glucose levels) to detect glucose levels in the eye.

An example apparatus for detecting blood glucose levels in a subject is described herein. The apparatus includes a thermographic imaging device configured to capture mid-infrared (MIR) electromagnetic emissions, and a computing device communicatively connected to the thermographic imaging device. The computing device includes a processor and memory operably connected to the processor, where the memory has computer-executable instructions stored thereon. The computing device is configured to receive a plurality of images of the subject's eye captured by the thermographic imaging device, calculate an average radiance value for a pixel region of interest using the plurality images of the subject's eye, correct the average radiance value for the pixel region of interest based on a temperature of the subject's eye at the time of image capture, and correlate the corrected average radiance value for the pixel region of interest to a blood glucose value of the subject.

In some implementations, the plurality of images is four images.

Alternatively or additionally, the MIR electromagnetic emissions are in a wavelength range from about 9 μm to about 11 μm. Optionally, the MIR electromagnetic emissions are in a wavelength range from about 9.7 μm to about 10.3 μm.

Alternatively or additionally, the step of calculating the average radiance value for the pixel region of interest includes calculating a respective average radiance value in the pixel region of interest for each of the plurality of images. The average radiance value for the pixel region of interest is an average value of the respective average radiance values.

Alternatively or additionally, the thermographic imaging device is an infrared camera. In some implementations, the thermographic imaging device is a microbolometer. Optionally, the microbolometer is a vanadium oxide (VOX) or amorphous silicon (a-Si) microbolometer. Alternatively or additionally, the microbolometer includes a focal plane array of about 100×100 active pixels.

Alternatively or additionally, the step of correcting the average radiance value for the pixel region of interest based on the temperature of the subject's eye at the time of image capture includes scaling the average radiance value for the pixel region of interest to a corresponding radiance value at about 33.5° C.

Alternatively or additionally, the step of correlating the corrected average radiance value for the pixel region of interest to the blood glucose value of the subject includes querying a database to obtain the blood glucose value of the subject corresponding to the corrected average radiance value for the pixel region of interest.

Alternatively or additionally, the step of correlating the corrected average radiance value for the pixel region of interest to the blood glucose value of the subject further includes using a search algorithm to identify a most probable blood glucose value of the subject corresponding to the corrected average radiance value for the pixel region of interest.

Alternatively or additionally, the apparatus further includes a frame configured to align a sensor of the thermographic imaging device in front of the subject's eye, and a collimating ring limiting a field of view of the sensor to a defined region about the center of the subject's eye. The collimating ring defines the distance from the detector to the subject's eye.

Alternatively or additionally, the system is incorporated into a handheld electronic device.

An example method for detecting blood glucose levels in a subject is described herein. The method includes capturing, using a thermographic imaging device, a plurality of images of the subject's eye, calculating, using a computing device, an average radiance value for a pixel region of interest based on the plurality images of the subject's eye, correcting, using the computing device, the average radiance value for the pixel region of interest based on a temperature of the subject's eye at the time of image capture, and correlating, using the computing device, the corrected average radiance value for the pixel region of interest to a blood glucose value of the subject.

In some implementations, the method further includes transmitting the plurality of images of the subject's eye to the computing device over a communication link.

In some implementations, the method further includes assaying a blood sample from the subject to measure blood glucose level if an abnormal glucose value is returned in response the correlation step.

In some implementations, the method further includes adjusting glucose level in the subject based on the glucose value returned in response the correlation step.

Another example method for detecting blood glucose levels in a subject is described herein. The method includes passively quantifying mid-infrared (MIR) electromagnetic emissions from the eye of the subject, and comparing the MIR emissions to standard control values to estimate glucose levels in the eye.

In some implementations, the MIR emissions are detected at a wavelength of about 8 to 11 μm. Optionally, the MIR emissions are detected at a wavelength of about 10 μm.

Alternatively or additionally, the MIR emissions are detected using a bolometer-type infrared imaging device.

Alternatively or additionally, the MIR emissions are detected using a microbolometer infrared camera.

Alternatively or additionally, the method includes assaying a blood sample from the subject to measure blood glucose levels if abnormal glucose levels are estimated.

Alternatively or additionally, the method further includes adjusting glucose levels in the subject based on the estimated glucose levels.

An example blood-glucose detection apparatus is described herein. The apparatus includes a mid-infrared (MIR) electromagnetic emissions sensor having a field of view, a frame configured to align the sensor in front of a subject's eye, a collimating ring limiting the field of view to a defined region about the center of the eye, and a processor and computerized memory configured to measure blood glucose concentration in the subject by initiating computer implemented instructions. The collimating ring defines the distance from the detector to the subject's eye. The processor is configured to store a set of standard control values, where the set of standard control values include a respective average of control voltage values induced at pixels of the mid-infrared radiation (MIR) sensor for MIR emitted through respective transmission media having known glucose concentrations, store, during a measurement cycle, voltage measurements corresponding to each voltage induced by mid-infrared radiation (MIR) emitted from the eye and incident upon the pixels, integrate the voltage measurements and produce a single voltage value for the measurement cycle, calculate an average voltage measurement of the single voltage measurements across a plurality of measurement cycles, and correlate the average voltage measurement to the known blood glucose concentration having a control voltage value equal to the average voltage measurement.

Alternatively or additionally, the collimating ring is made of a material having an emissivity of about 1.

Alternatively or additionally, the apparatus further includes a continuous medicament delivery device in data communication with the apparatus, configured to receive the blood glucose value from the apparatus, and further configured to deliver insulin to the subject for glucose control.

Another example blood-glucose detection apparatus is described herein. The apparatus includes a mid-infrared (MIR) electromagnetic emissions sensor having a field of view, a frame configured to align the sensor in front of a subject's eye, a collimating ring limiting the field of view to a defined region about the center of the eye, and a processor and computerized memory configured to measure blood glucose concentration in the subject by initiating computer implemented instructions. The collimating ring defines the distance from the detector to the subject's eye. The processor is configured to store a set of standard control values including average control radiance values, for a selected wavenumber, induced at the pixels for MIR emitted through respective transmission media having known glucose concentrations, where the control values are accessible by the processor, receive, in a measurement cycle utilizing the selected wavenumber, a radiance measurement corresponding to MIR incident upon each of the respective pixels, calculate an average radiance measurement from the respective radiance measurements corresponding to respective measurement cycles in a plurality of measurement cycles, and correlate the average radiance measurement to the known glucose concentration having a control radiance value equal to the average radiance measurement.

Another example method of measuring blood glucose concentration is described herein. The method includes storing a set of standard control values, where the set of standard control values includes a respective average of control voltage values induced at pixels of a mid-infrared radiation (MIR) sensor for MIR emitted through respective transmission media having known glucose concentrations, storing, during a measurement cycle, voltage measurements corresponding to each voltage induced by mid-infrared radiation (MIR) emitted from the eye and incident upon the pixels, integrating the voltage measurements and producing a single voltage value for the measurement cycle, calculating an average voltage measurement of the single voltage measurements across a plurality of measurement cycles, and correlating the average voltage measurement to the known blood glucose concentration having a control voltage value equal to the average voltage measurement.

Alternatively or additionally, voltages at the pixels are normalized to reference values calculated as reference voltages induced at pixels by a black body reference emission of MIR.

An example optical glucometer is described herein. The optical glucometer includes a mid-infrared (MIR) sensor including an array of pixels connected to a processor that correlates blood glucose values to voltage readings induced by MIR incident upon the respective pixels, and computer memory connected to the processor, the computer memory storing a set of control values including a respective average of control voltage values induced at the pixels for MIR emitted through known glucose concentrations, where the control values are accessible by the processor. The processor is configured to receive in a measurement cycle voltage measurements corresponding to each voltage induced by MIR incident upon the respective pixels, integrate the voltage measurements and produce a single voltage value for the measurement cycle, calculate an average voltage measurement from the single voltage values corresponding to respective measurement cycles in a plurality of measurement cycles, and correlate the average voltage measurement to the known glucose concentration stored in the memory having a control voltage value equal to the average voltage measurement.

Another example optical glucometer is described herein. The optical glucometer includes an infrared camera including an array of pixels connected to a processor that correlates blood glucose values to radiance measurements induced by mid-infrared radiation (MIR) incident upon the respective pixels, and computer memory connected to the processor, the computer memory storing a set of standard control values including average control radiance values, for a selected wavenumber, induced at the pixels for MIR emitted through respective transmission media having known glucose concentrations, where the control values are accessible by the processor. The processor is configured to receive, in a measurement cycle utilizing the selected wavenumber, a radiance measurement corresponding to MIR incident upon each of the respective pixels, calculate an average radiance measurement from the respective radiance measurements corresponding to respective measurement cycles in a plurality of measurement cycles, and correlate the average radiance measurement to the known glucose concentration having a control radiance value equal to the average radiance measurement.

In some implementations, the array of pixels is configured to transmit a thermal image of an eye to the processor, and the processor is configured to convert the thermal image to a grayscale image of radiance values.

In some implementations, the processor is configured to receive the radiance measurements for a subset of pixels corresponding to a localized section of an image of eye and multiply the respective radiance measurements for each pixel by a corresponding grayscale image value prior to calculating the average.

In some implementations, radiance values at the pixels are normalized to reference values calculated as reference radiance values induced at pixels by a black body reference emission of MIR.

An example method of measuring blood glucose concentration in eye is described herein. The method includes storing a set of standard control values, where the set of standard control values includes average control radiance values, for a selected wavenumber, induced at pixels of a mid-infrared radiation (MIR) sensor for MIR emitted through respective transmission media having known glucose concentrations, storing, during a measurement cycle, radiance measurements corresponding to mid-infrared radiation (MIR) emitted from the eye and incident upon the pixels, calculating an average radiance measurement from the respective radiance measurements corresponding to respective measurement cycles in a plurality of measurement cycles, and correlating the average radiance measurement to the known blood glucose concentration having an average control radiance value equal to the average radiance measurement.

In some implementations, the wavenumber is 1030 cm$^{-1}$ or 1078 cm$^{-1}$.

In some implementations, the method further includes extracting from a thermal image of the pixels the average radiance measurement and a temperature value for a localized area of the pixels.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

The details of one or more embodiments of the invention are set forth in the accompanying drawings and the description below. Other features, objects, and advantages of the invention will be apparent from the description and drawings, and from the claims.

DESCRIPTION OF DRAWINGS

The components in the drawings are not necessarily to scale relative to each other. Like reference numerals designate corresponding parts throughout the several views.

FIG. 6C shows the shutter upper part. FIG. 6D shows the shutter lower part.

FIG. 31 illustrates images of a black body reference and a patient's eye captured using an apparatus described with respect to FIGS. 6B-6D.

FIGS. 36A-36D illustrate an example handheld optical glucometer.

DETAILED DESCRIPTION

Figure 1:
FIG. 1 is a thermal image showing spatial resolution of radiance and temperature responses possible using a mid-infrared (MIR) camera to image the eye with a spectral region of 8 to 12 microns, centered on 10 microns.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Disclosed are non-invasive optical means of determining blood glucose levels in diabetics that can replace the current finger stick technology. This would eliminate the need for test strips used with glucometers and would be far less painful. This also cuts the cost of monitoring the glucose and would allow for more frequent monitoring of the blood glucose level, which is vital for diabetic self-monitoring and control.

Glucose is present in fluid films (tears) on the eyeball surface. Glucose is also present in the eye lens and can cause changes in the shape of the lens. As disclosed herein, the amount of glucose in the eye fluid film can be determined by quantifying mid-infrared (MIR) electromagnetic emissions. Using controlled test solutions, the MIR, centered around 10 microns, was found to be effective for this purpose.

Therefore, in some embodiments, the presence of glucose is indicated by MIR emitted by the eyeball surface. These emissions occur because the eye is warm and radiation is being recorded from a warm blackbody filtered by the film that contains the glucose. No laser or light source is directed onto the eye to develop/reflect a signal. So this is a completely passive and non-invasive technology.

In some embodiments, the methods and devices quantify MIR emissions in the eye at wavelengths from about 8 to 11 μm, including from about 9.6 μm to about 11 μm, from about 9.8 to about 10 μm. In some implementations, the methods and devices quantify MIR emissions in the eye at wavelengths from about 9.7 μm to about 10.3 μm. Additional wavelengths can be detected; however past 11 microns water absorbs more IR radiation and therefore reduces signal transmission. Going as low as 8 microns also reduces the signal as glucose becomes less absorbing.

In some embodiments, MIR radiation is detected using one or more bolometer-type infrared imaging devices (e.g. microbolometer) measuring voltage, current, or a combination thereof. In some cases, the bolometer-type infrared imaging device is centered on the 10 micron region.

For example, Micro-Epsilon of Ortenburg, Germany manufactures a THERMOMETER CS compact infrared (IR) sensor with integral controller, which has as spectral range of 8 to 14 μm and optional resolution of 15:1. The Bolometric sensor can integrate the infrared radiation across the total eye surface and the sensor and amplifier produce a single voltage value. In one non-limiting example, these values can be recorded at 100 Hz over a 2 second period. Many recording rates and time intervals are possible as long as a sufficient number of readings, e.g., 100 readings, are acquired. A sufficiently large sample size improves the noise suppression and the average accuracy.

These readings can then be averaged to produce the output. The eye is generally located when a few centimeters of the detector lens.

In some embodiments, MIR radiation is detected using a microbolometer infrared camera. A microbolometer is a specific type of bolometer used as a detector in a thermal camera. Infrared radiation with wavelengths between 7.5-14 µm strikes the detector material, heating it, and thus changing its electrical resistance. This resistance change is measured and processed into temperatures which can be used to create an image.

A microbolometer consists of an array of pixels, each pixel being made up of several layers. Each company that manufactures microbolometers has their own unique procedure for producing them and they even use a variety of different absorbing materials. In some cases, the bottom layer consists of a silicon substrate and a readout integrated circuit (ROIC). Electrical contacts are deposited and then selectively etched away. A reflector, for example, a titanium mirror, is created beneath the IR absorbing material. Since some light is able to pass through the absorbing layer, the reflector redirects this light back up to ensure the greatest possible absorption, hence allowing a stronger signal to be produced. Next, a sacrificial layer is deposited so that later in the process a gap can be created to thermally isolate the IR absorbing material from the ROIC. A layer of absorbing material is then deposited and selectively etched so that the final contacts can be created. To create the final bridge like structure, the sacrificial layer is removed so that the absorbing material is suspended approximately 2 µm above the readout circuit. Because microbolometers do not undergo any cooling, the absorbing material must be thermally isolated from the bottom ROIC and the bridge like structure allows for this to occur. After the array of pixels is created the microbolometer is encapsulated under a vacuum to increase the longevity of the device. In some cases the entire fabrication process is done without breaking vacuum.

The quality of images created from microbolometers has continued to increase. The microbolometer array is commonly found in two sizes, 320×240 pixels or less expensive 160×120 pixels. Current technology has led to the production of devices with 640×480 or 1024×768 pixels. There has also been a decrease in the individual pixel dimensions. The pixel size was typically 45 µm in older devices and has been decreased to 17 µm in current devices. As the pixel size is decreased and the number of pixels per unit area is increased proportionally, an image with higher resolution is created, but with a higher NETD (Noise Equivalent Temperature Difference (differential)) due to smaller pixels being less sensitive to IR radiation.

The two most commonly used IR radiation detecting materials in microbolometers are amorphous silicon (a-Si) and vanadium oxide (VOX). Other materials that have been investigated include: titanium (Ti), yttrium barium copper oxide (YBaCuO), germanium silicon oxide (GeSiO), poly silicon germanium (SiGe), bismuth lanthanum strontium manganese oxide (BiLaSrMnO), and a protein based cytochrome C and bovine serum albumin. Amorphous Si (a-Si) works well because it can easily be integrated into the complementary metal oxide semiconductor (CMOS) fabrication process, is highly stable, a fast time constant, and has a long mean time before failure. To create the layered structure and patterning, the CMOS fabrication process can be used but it requires temperatures to stay below 200° C. on average. A problem with some potential materials is that to create the desirable properties their deposition temperatures may be too high although this is not a problem for a-Si thin films. a-Si also possesses excellent values for thermal coefficient of resistance (TCR), 1/f noise and resistance when the deposition parameters are optimized.

Vanadium oxide thin films may also be integrated into the CMOS fabrication process although not as easily as a-Si for temperature reasons. VOX is an older technology than a-Si, and for these reasons its performance and longevity are less. Deposition at high temperatures and performing post-annealing allows for the production of films with superior properties although acceptable films can still be made subsequently fulfilling the temperature requirements. $VO_2$ has low resistance but undergoes a metal-insulator phase change near 67° C. and also has a lower value of TCR. On the other hand, $V_2O_5$ exhibits high resistance and also high TCR. Many phases of VOX exist although it seems that x≈1.8 has become the most popular for microbolometer applications.

Most microbolometers can contain a temperature sensitive resistor which makes them a passive electronic device. In some cases, the microbolometers use a thin film transistor (TFT), which is a special kind of field effect transistor. The main change in these devices would be the addition of a gate electrode. Although the main concepts of the devices are similar, using this design allows for the advantages of the TFT to be utilized. Some benefits include tuning of the resistance and activation energy and the reduction of periodic noise patterns. As of 2004 this device was still being tested and was not used in commercial IR imaging.

Figure 4:
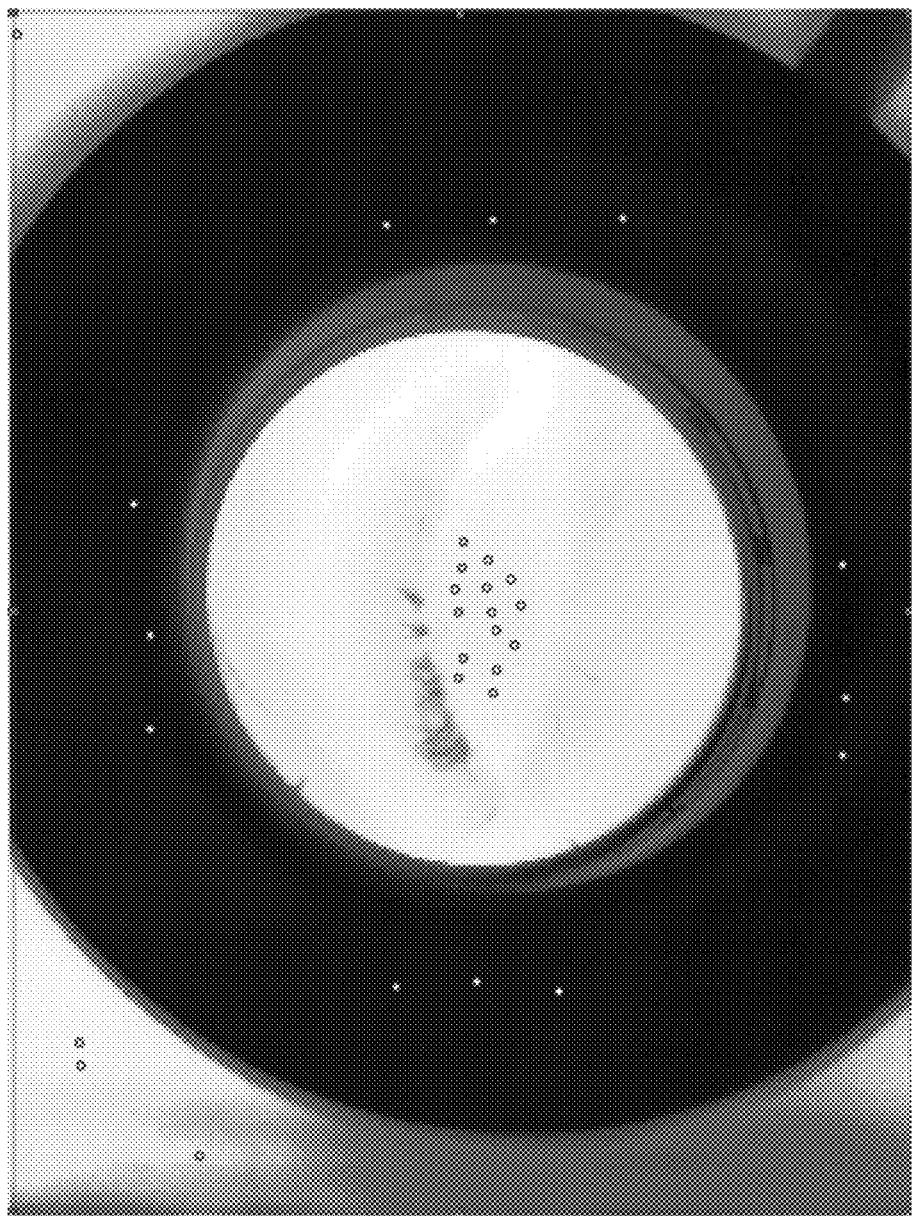
FIG. 4 is a thermal image of an eye taken with an MIR camera. The dark ring around the eye is used as a reference. The small dots are measurement points where pixel values are obtained in three colors. The total value corresponds to MIR energy emitted per pixel.

For example, FLIR Systems, Inc. of Wilsonville. Oreg. manufactures an uncooled microbolometer infrared camera (FLIR A325sc) with a 320×240 long wavelength (LWIR) resolution and a spectral range of 7.5 to 13.0 µm. In these embodiments, the infrared camera has a lens that allows one to focus more directly on the eye and the reference ring. In some cases, a rectangular region of an infrared sensor is positioned to cover the eye such that the eye is properly within the infrared camera field of view. This can, for example, include about 400 pixels, e.g., about 10 by 40 pixels. This can be used to obtain the average radiance values. The region of the infrared sensor dedicated to imaging an eyeball may vary in size and shape as necessary for patient anatomy, ambient lighting, sample sizes, and camera parameters typically adjusted for test conditions. In this regard, the set of pixels sensitive to the eye may be circular, elliptical, or other convenient shapes that allow for data collection under the circumstances at hand. As shown in FIG. 4, the sensor gathers sufficient image data to provide a desirable number of radiance and/or temperature readings from select positions on and around the eye, particularly in the center of the eye. The number of readings shown in FIG. 4 is not limiting of the readings available for analysis, and in one non-limiting example, at least 50 readings may be gathered across the center of the surface of the eye and the optical film thereon. Tracking the region from which radiance and temperature readings have been gathered is, furthermore, useful in creating a software mask for acquiring normalized data readings across the sensor, thereby receiving the necessary temperature and radiance data.

Infrared imaging has a much higher spatial resolution. It offers enhanced temperature resolution as well, which is not provided by the bolometer. It can also output data as red/green/blue images along with data files from the image presented in terms of radiance data (Watts/square cm per steradian) and temperatures, degrees Celsius, for each pixel. This camera was used to confirm bolometric observations and to search for strategies to determine the glucose values from the eye. Eye temperatures vary but the glucose solution appears to be uniform across the eye.

Infrared imaging can be used instead of, or as a confirmation of, bolometric data. Infrared imaging also allows for detection of glucose distribution across the eye surface. Infrared imaging is more sensitive but the bolometer is sensitive enough and may be cheaper and less complicated in a medical device.

In some embodiments, the device quantifies pixel values representing MIR emissions at a plurality of pre-determined or random points in the eye. In some cases, the device measures pixel values across the entire image of the lens, or some subset thereof (also referred to herein as a "pixel region of interest").

Figure 6A:
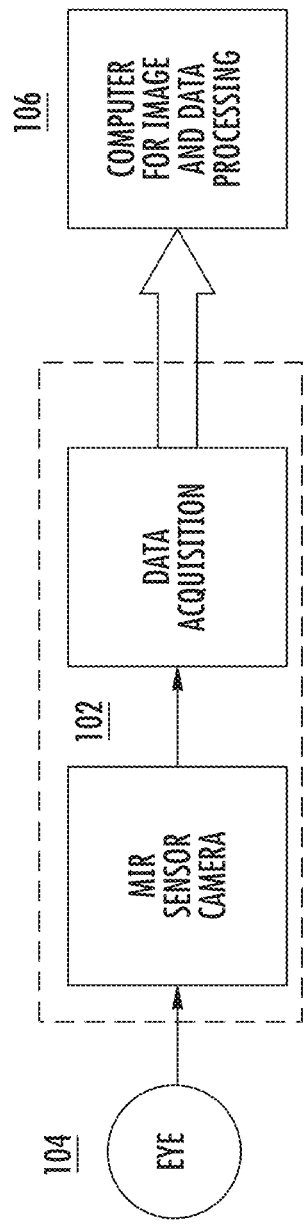
FIG. 6A is a block diagram of an example optical glucometer having a mid-range infrared, MIR, sensor/imaging system for glucose level measurement in the eye surface fluid according to one implementation described herein.

Referring now to FIG. 6A, a block diagram of an example optical glucometer having a MIR sensor/imaging system for glucose level measurement in the eye surface fluid is shown. The optical glucometer can include a thermographic imaging device 102 configured to capture MIR electromagnetic emissions. The thermographic imaging device 102 can be used to capture one or more images of a subject's eye 104. For example, the thermographic imaging device 102 can be an infrared camera such as a bolometric-type or microbolometric-type device as described herein. As shown in FIG. 6A, the thermographic imaging device 102 can include a MIR sensor and data acquisition hardware/software (e.g., microprocessor, analog-to-digital converter, filters, amplifiers, etc.). As described herein, the MIR sensor can be configured for peak sensitivity at wavelengths in a range from about 9 μm to about 11 μm. In some implementations, the MIR sensor can be configured for peak sensitivity at wavelengths in a range from about 9.7 μm to about 10.3 μm. This can be accomplished using the native detector sensitivity of a MIR sensor and/or with hardware/software. These wavelength ranges overlap with 9-10 μm where glucose in the eye film acts as a filter that inhibits the transmission of light. Glucose inhibits transmission of IR light with peaks of specific interest at 9.7 and 10.3 μm. It should be understood that the MIR sensor can be configured for peak sensitivity at wavelengths in ranges other than those provided above as examples.

Bolometers and microbolometers are known in the art. Bolometers include, but are not limited to, the FLIR A325sc thermal imaging camera from FLIR Systems, Inc. of Wilsonville, Oreg., which is provided only as an example. Microbolometers include, but are not limited to, the FLIR LEPTON thermal imaging camera from FLIR Systems, Inc. of Wilsonville. Oreg, which is provided only as an example. The FLIR LEPTON camera is a LWIR camera with a relatively small IR camera (i.e., smaller than a dime) as compared to a bolometer and can be incorporated into handheld electronic devices such a smartphone or tablet or optical glucometer. The FLIR LEPTON camera uses a focal plane array of 160×120 or 80×60 active pixels, which facilitates incorporation into a handheld device. Although the FLIR LEPTON camera is configured for uncooled thermal imaging, this disclosure contemplates that the images can be calibrated using a black body reference as described in Example 3. It should be understood that the FLIR A325sc and LEPTON cameras are only provided as example bolometers and microbolometers, respectively. This disclosure contemplates using other bolometers and/or microbolometers than those provided as examples. For example, in some implementations, a microbolometer with a focal plane array of about 100×100 pixels can be used. With this type of resolution, it is possible to achieve sufficient signal-to-noise enhancement. The optical glucometer can also include a computing device 106. For example, the computing device 106 can be the example computing device as described with regard to FIG. 6E. The thermographic imaging device 102 and the computing device 106 can be communicatively coupled, for example, by one or more communication links. This disclosure contemplates the communication links are any suitable communication link. For example, a communication link may be implemented by any medium that facilitates data exchange between the thermographic imaging device 102 and the computing device 106 including, but not limited to, wired, wireless and optical links. Example communication links include, but are not limited to, an internal data bus, a LAN, a WAN, a MAN, Ethernet, the Internet, or any other wired or wireless link such as WiFi, WiMax, 3G or 4G It should be appreciated that the logical operations described herein with respect to the various figures may be implemented (1) as a sequence of computer implemented acts or program modules (i.e., software) running on a computing device (e.g., the computing device described in FIG. 6E). (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 6B:
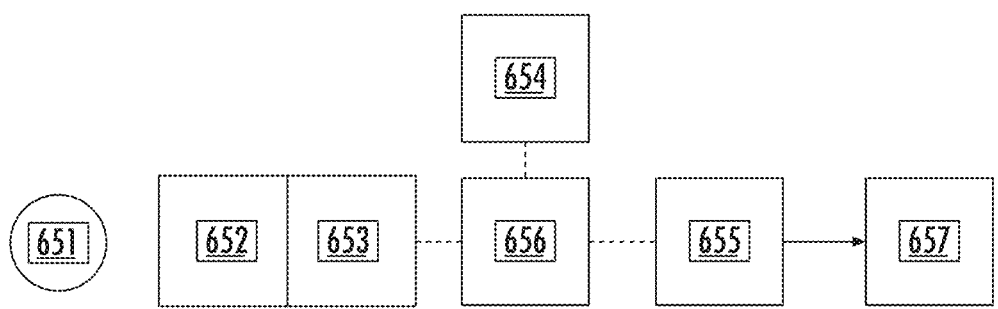
FIG. 6B is a block diagram of an example optical glucometer with a FLIR LEPTON camera or glucose level measurement in the eye surface fluid according to one implementation described herein.
Figure 6C:
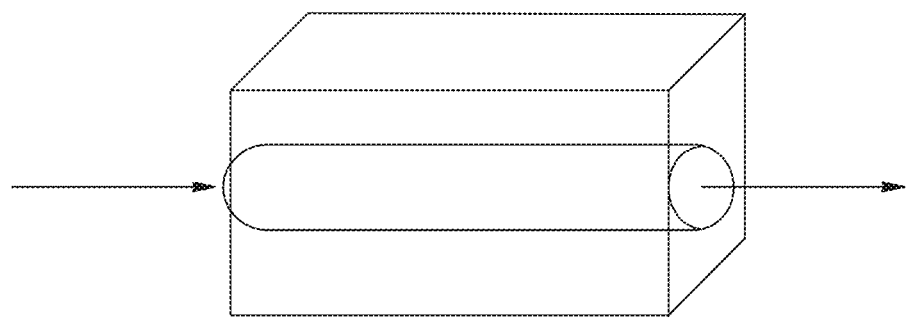
FIGS. 6C and 6D illustrates aspects of the example optical glucometer shown in FIG. 6B.
Figure 6D:
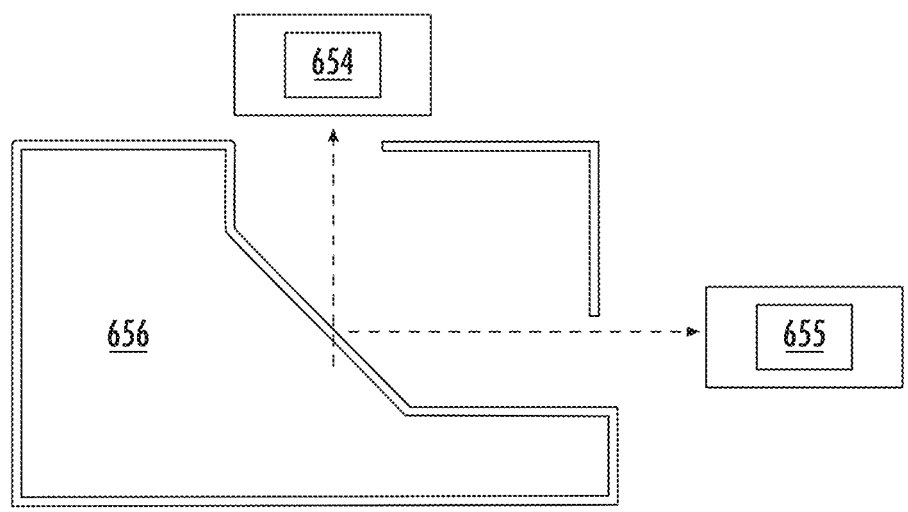
Figure 6E:
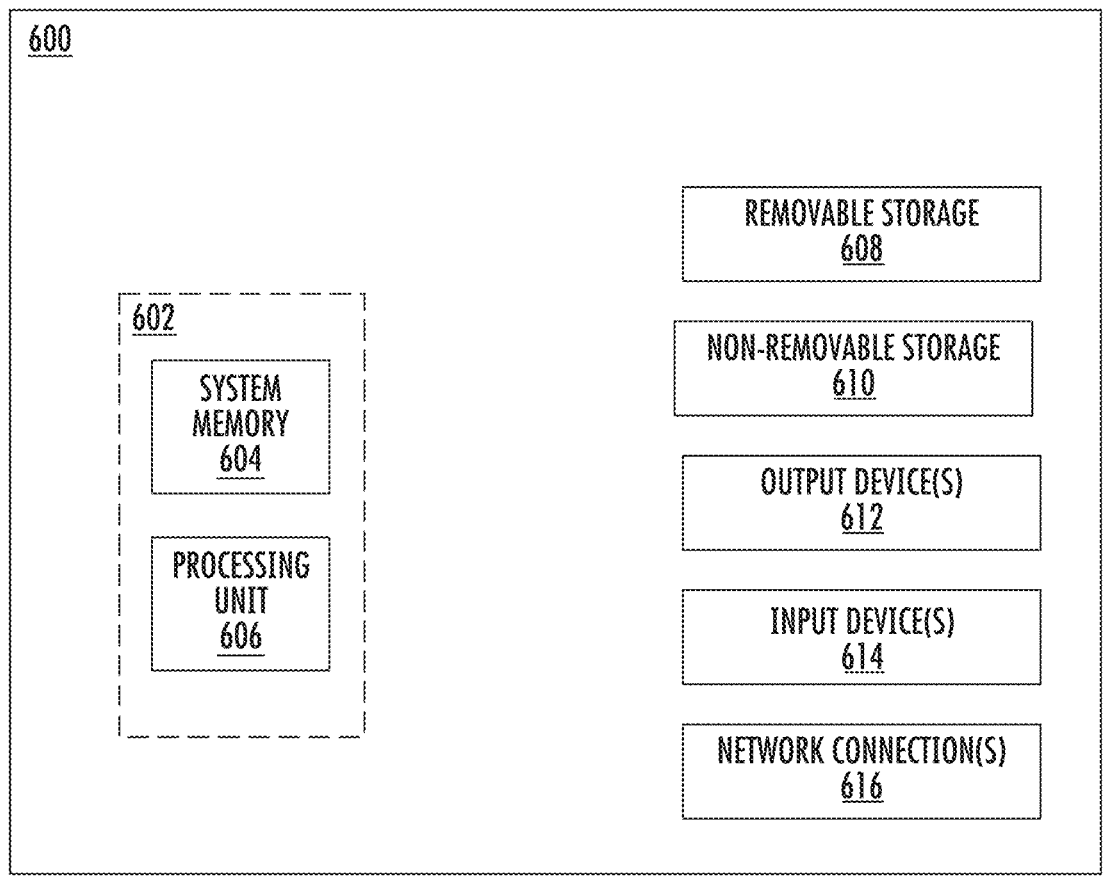
FIG. 6E is a block diagram of an example computing device.

Referring to FIG. 6E, an example computing device 600 upon which embodiments of the invention may be implemented is illustrated. It should be understood that the example computing device 600 is only one example of a suitable computing environment upon which embodiments of the invention may be implemented. Optionally, the computing device 600 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In its most basic configuration, computing device 600 typically includes at least one processing unit 606 and system memory 604. Depending on the exact configuration and type of computing device, system memory 604 may be volatile (such as random access memory (RAM)), non-volatile (such as read-only memory (ROM), flash memory, etc.), or some combination of the two. This most basic configuration is illustrated in FIG. 6E by dashed line 602. The processing unit 606 may be a standard programmable processor that performs arithmetic and logic operations necessary for operation of the computing device 600. The computing device 600 may also include a bus or other communication mechanism for communicating information among various components of the computing device 600.

Computing device 600 may have additional features/functionality. For example, computing device 600 may include additional storage such as removable storage 608 and non-removable storage 610 including, but not limited to, magnetic or optical disks or tapes. Computing device 600 may also contain network connection(s) 616 that allow the device to communicate with other devices. Computing device 600 may also have input device(s) 614 such as a keyboard, mouse, touch screen, etc. Output device(s) 612 such as a display, speakers, printer, etc. may also be included. The additional devices may be connected to the bus in order to facilitate communication of data among the components of the computing device 600. All these devices are well known in the art and need not be discussed at length here.

The processing unit 606 may be configured to execute program code encoded in tangible, computer-readable media. Tangible, computer-readable media refers to any media that is capable of providing data that causes the computing device 600 (i.e., a machine) to operate in a particular fashion. Various computer-readable media may be utilized to provide instructions to the processing unit 606 for execution. Example tangible, computer-readable media may include, but is not limited to, volatile media, non-volatile media, removable media and non-removable media implemented in any method or technology for storage of information such as computer readable instructions, data structures, program modules or other data. System memory 604, removable storage 608, and non-removable storage 610 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 606 may execute program code stored in the system memory 604. For example, the bus may carry data to the system memory 604, from which the processing unit 606 receives and executes instructions. The data received by the system memory 604 may optionally be stored on the removable storage 608 or the non-removable storage 610 before or after execution by the processing unit 606.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Figure 17:
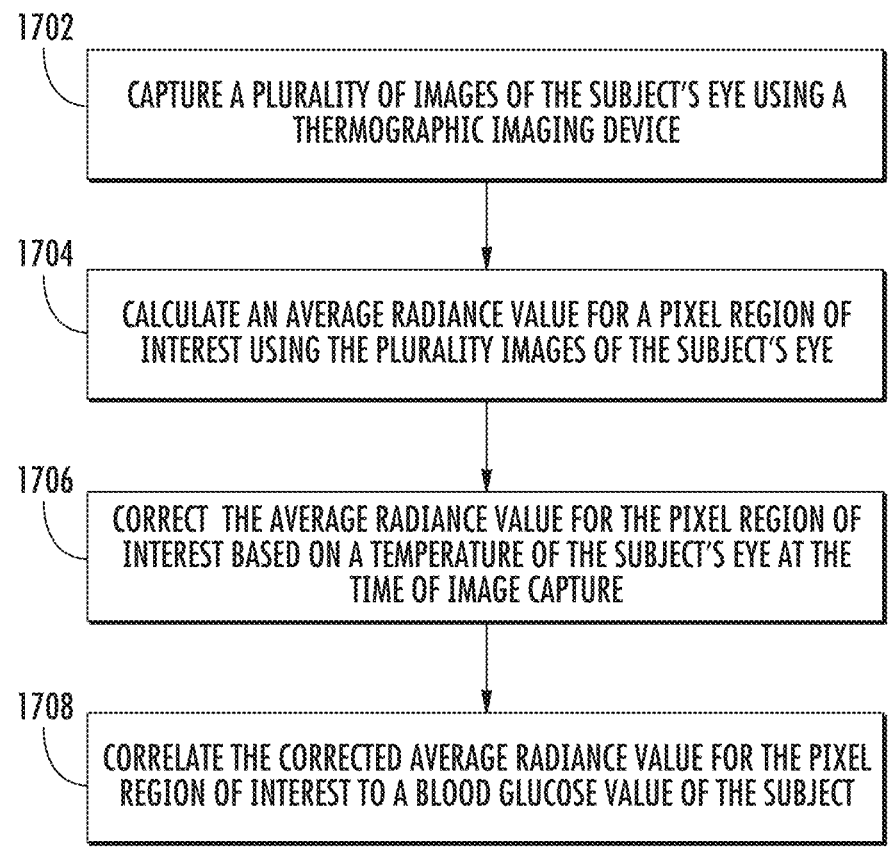
FIG. 17 illustrates example operations for detecting blood glucose levels of a patient according to one implementation described herein.

Referring now to FIG. 17, a flow diagram illustrating example operations for detecting glucose levels in a subject is shown. As described herein, the infrared radiation emitted by the human eye and filtered by glucose in the eye fluid film can be detected and correlated with standard finger stick blood glucose values, BGV. This disclosure contemplates that the operations can be implemented using the example optical glucometer (e.g., a patient self-monitoring system) described with respect to FIG. 6A or FIG. 6B, for example. At 1702, a plurality of images of the subject's eye can be captured using a thermographic imaging device (e.g., thermographic imaging device 102 of FIG. 6A or IR camera 655 of FIG. 6B). This disclosure contemplates capturing a plurality of images to reduce noise. For example, in some implementations, four images can be captured. Although four images is provided as an example, this disclosure contemplates capturing more or less than four images. It should be understood that there are tradeoffs between noise reduction and processing/storage requirements with an increasing number of images. The images can be transmitted from the thermographic imaging device to a computing device (e.g., computing device 600 of FIG. 6E) over a communication link for further processing.

At 1704, an average radiance value for a pixel region of interest can be calculated using the plurality images of the subject's eye. The pixel region of interest can optionally be a region of the infrared sensor positioned to cover a region of the subject's eye within a field of view of the thermographic imaging device. As described herein, the pixel region interest can have various sizes and/or shapes (e.g., circular, elliptical, or other convenient shapes), for example, tailored as necessary for patient anatomy, ambient lighting, sample sizes, and/or camera parameters. In an example implementation, the pixel region of interest can include 400 pixels, e.g., about 10 by 40 pixels, which is provided only as an example. This disclosure contemplates a pixel region of interest more or less than 400 pixels. To calculate the average radiance value for the pixel region of interest, a respective average radiance value for the pixels in each of the plurality of images can be calculated. This can be accomplished, for each image, by integrating the respective radiance value for each of the pixels in the pixel region of interest to obtain a single radiance value. The single average radiance value for each of the images can then be averaged to obtain the average radiance value for the pixel region of interest (i.e., a single average radiance value across all images).

At 1706, the average radiance value for the pixel region of interest can be corrected based on a temperature of the subject's eye at the time of image capture. As described below in Example 3, the average radiance value for the pixel region of interest can be scaled to a corresponding radiance value at about 33.5° C. This correction can compensate for the wavelength dependent response of the IR sensor of the thermographic imaging device.

At 1708, the corrected average radiance value for the pixel region of interest can be correlated to a blood glucose value of the subject. As described herein, the blood glucose value of the subject can be obtained by database lookup. Optionally, as described below in Example 3, a search algorithm can be used to identify a most probable blood glucose value of the subject corresponding to the corrected average radiance value for the pixel region of interest.

EXAMPLES

Example 1

Measurements were obtained using three IR sensor types. Two are bolometric-type devices, one measuring voltage and the other current, sensitive in the 8 to 12 micron regions and recording all radiation with a maximum sensitivity around 10 microns. These collected all of the MIR radiation along with the glucose signature. They were sensitive enough to observe changes in glucose levels, as indicated below. The optical configuration was such that the total eye was included in the radiation-collecting field.

The third device was an MIR camera that had high spatial resolution and hence point-by-point readings across the eye were possible. The spectral region was again 8 to 12 microns centered on 10 microns.

FIG. 1 illustrates the spatial resolution possible using an MIR camera. The dark disk is the reference for image-to-image comparison.

A large volume of warm solution in an MIR transparent bag was used to compare infrared radiation with concentrations. These solutions were not films, but rather bulk samples. FIGS. 2A to 2D illustrate the trends and demonstrate that there is a strong relationship between concentration and MIR signal detected using a bolometric detector.

Figure 2A:
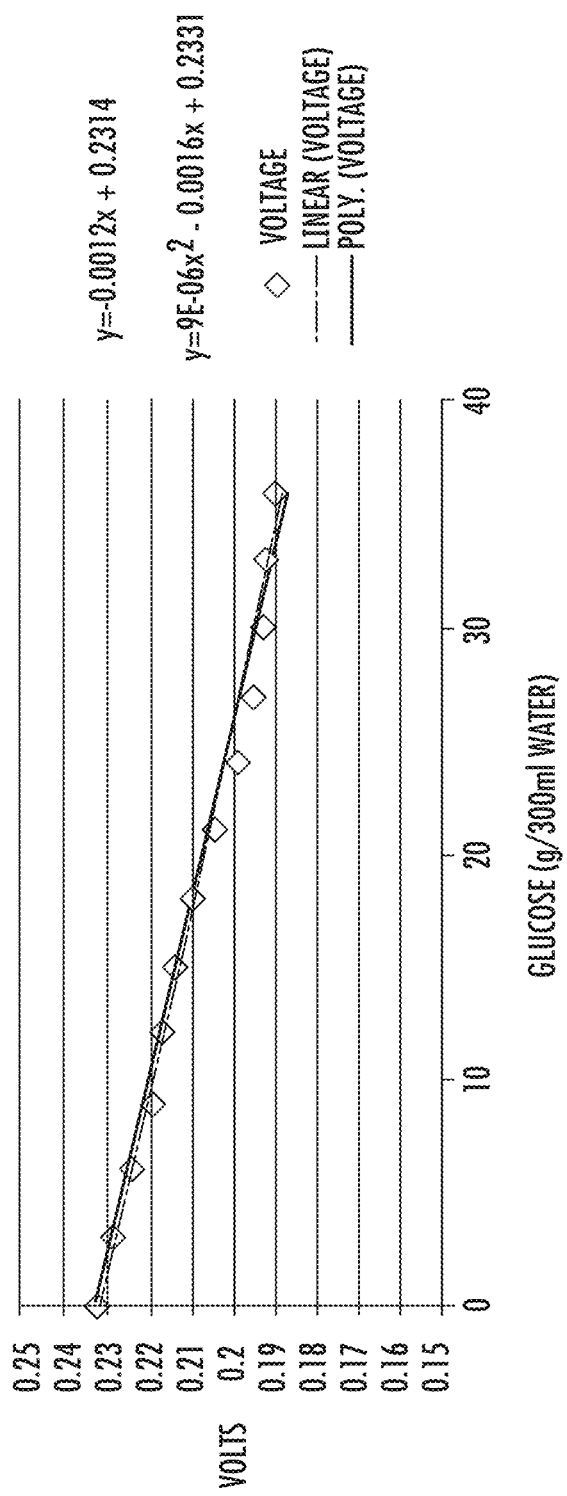
FIGS. 2A to 2D are graphs showing voltage (measured by MIR camera) as a function of glucose (g/300 ml water) for warm solutions of glucose in MIR transparent bags.
Figure 2B:
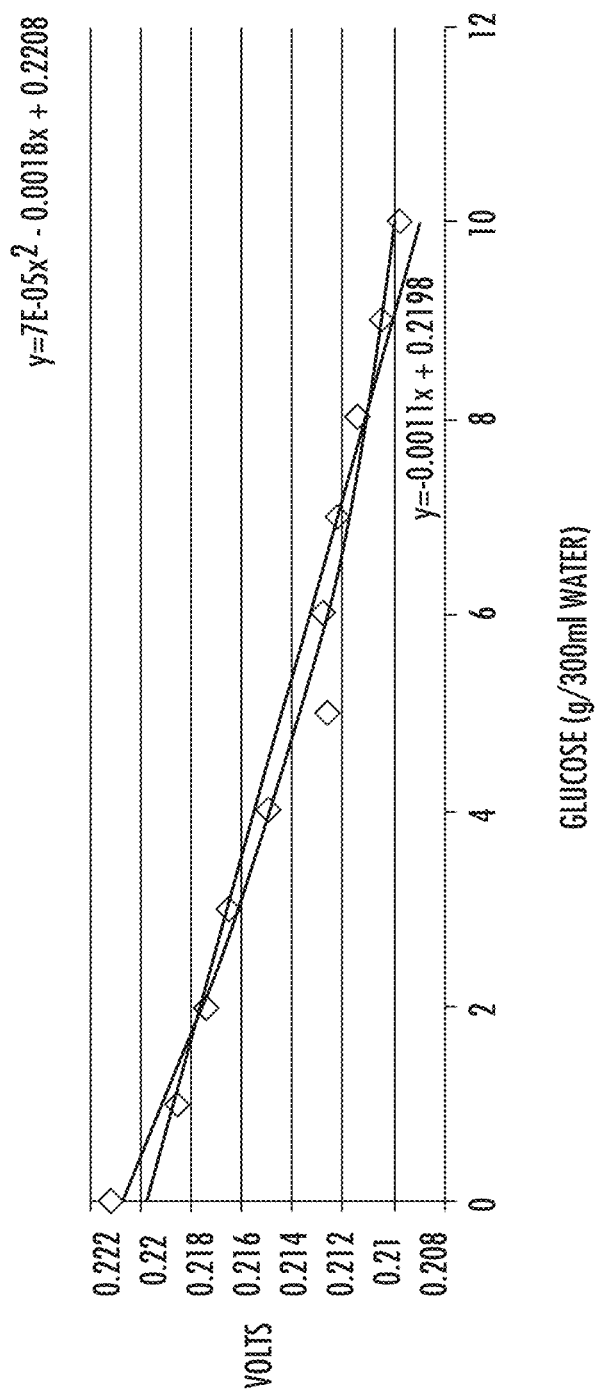
Figure 2C:
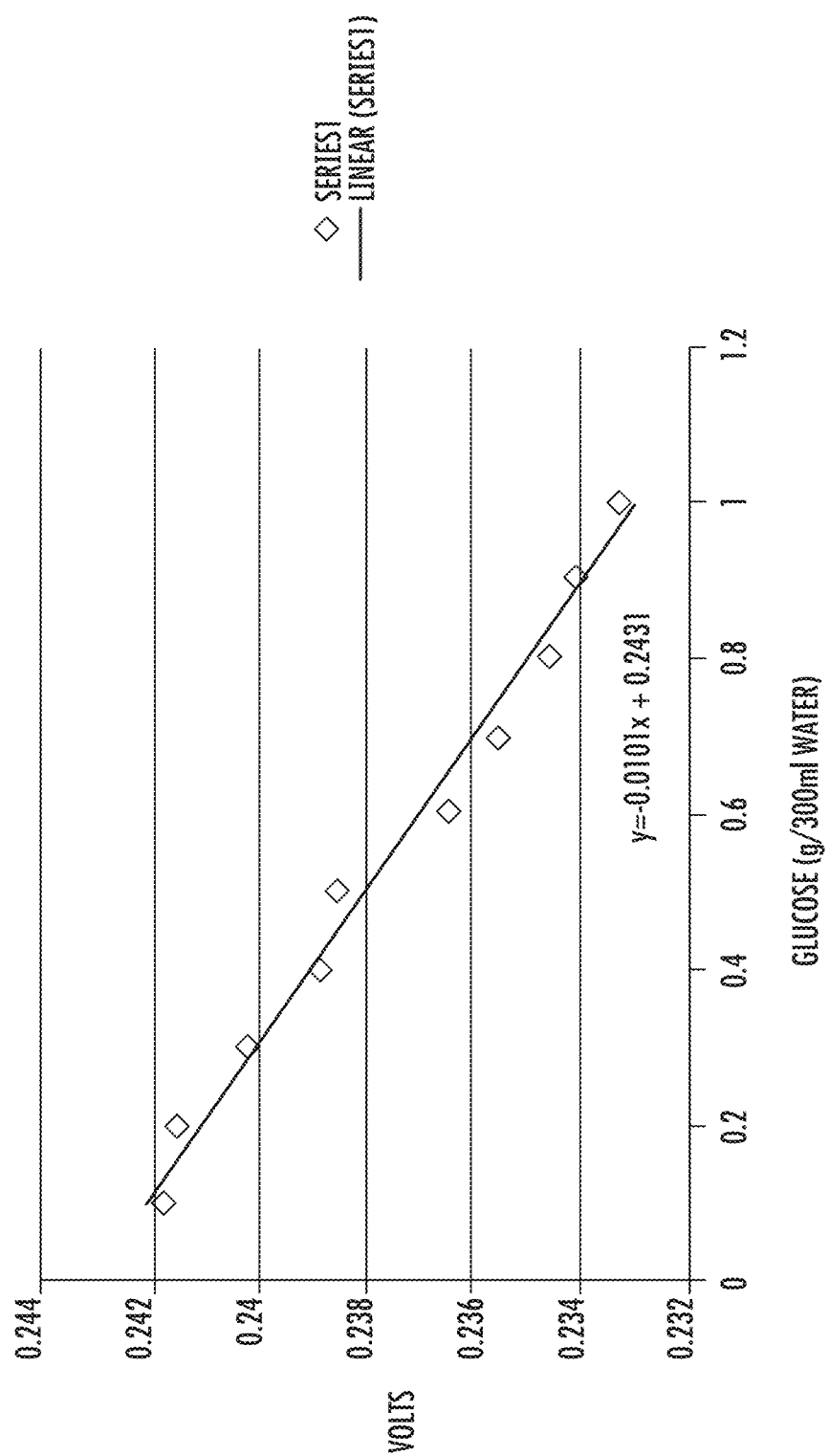
Figure 2D:
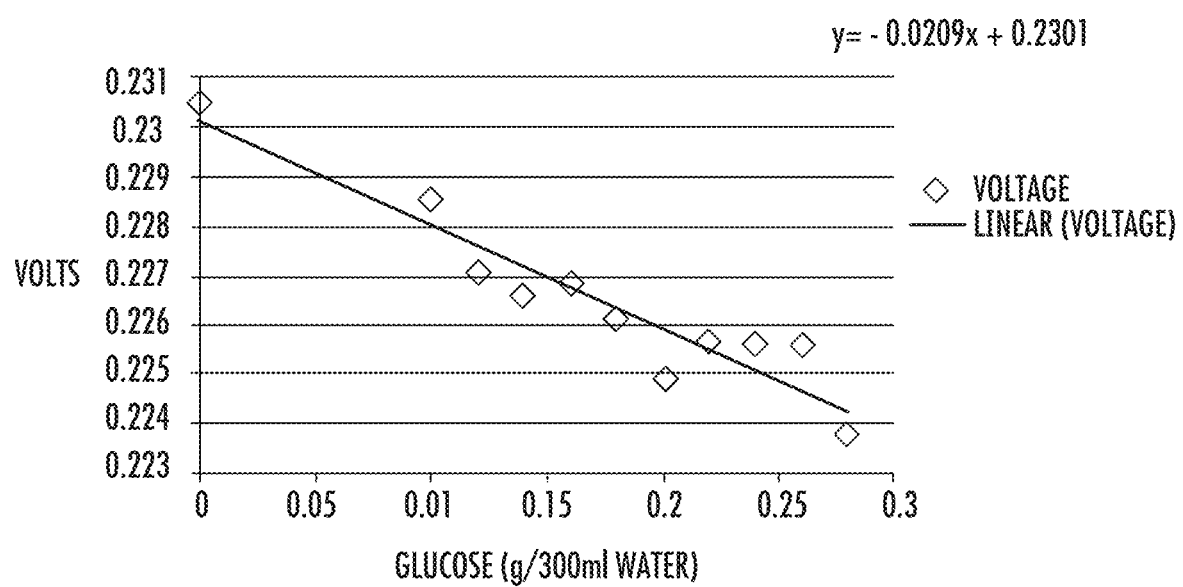

In FIGS. 2A to 2D, the vertical axis is in volts while the horizontal axis is in grams of glucose powder dissolved into 300 ml of water. Glucometers measure in milligrams per deciliter so this is a wide range. FIG. 2C covers the region over which a diabetic might expect to see their glucose values, i.e. ranging from about 67 to 300 mg/dL. FIG. 2D shows a more refined scale range from 16, a very low values for a patient, to 100 mg/dL.

Figure 3A:
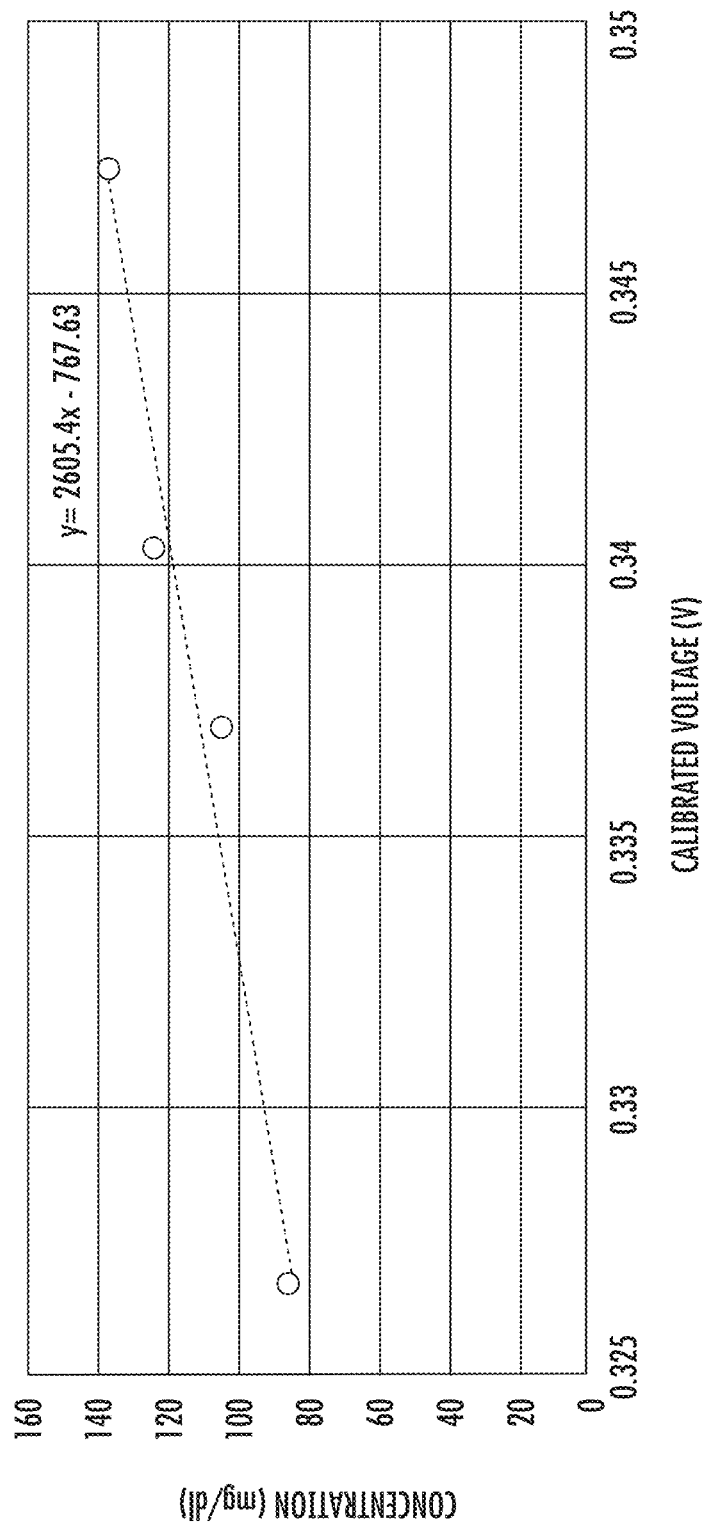
FIGS. 3A and 3B are graphs showing glucose concentration (mg/dl) as a function of voltage (measured by bolometric detector).
Figure 3B:
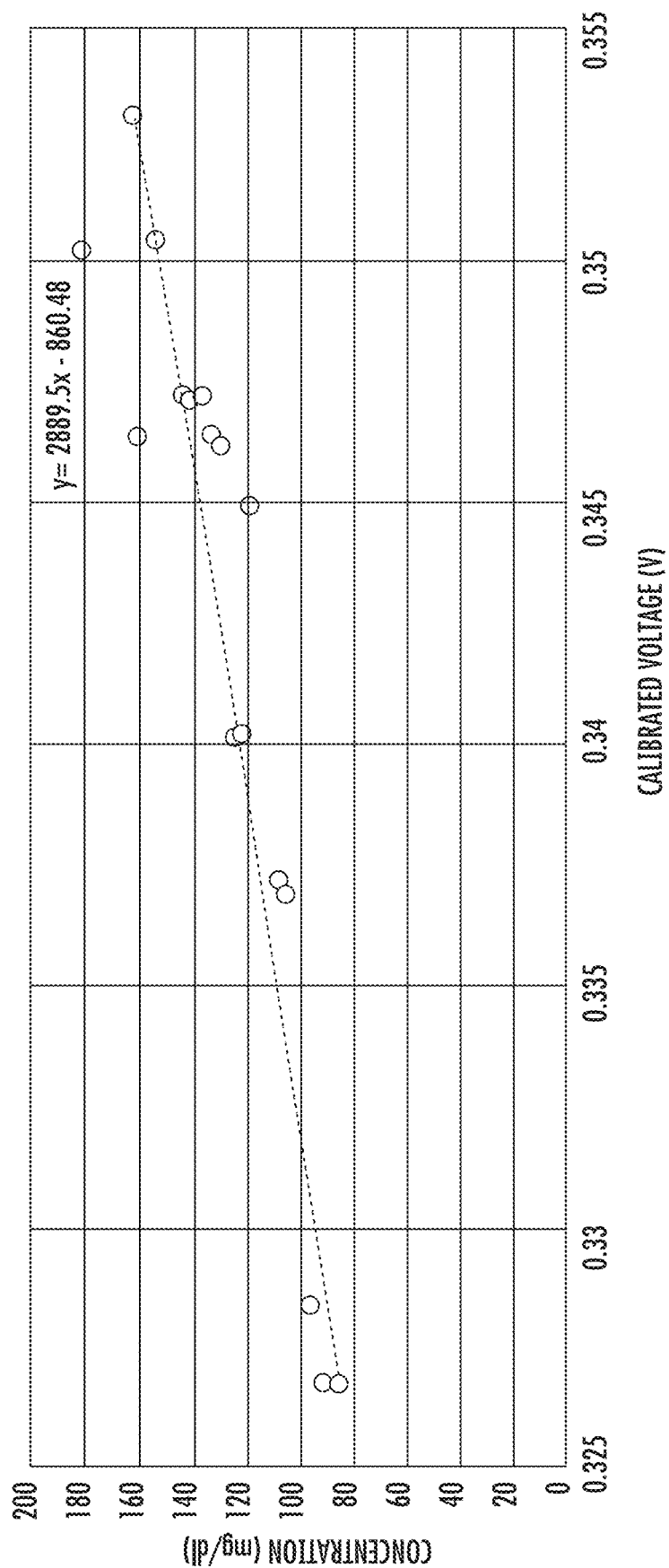

FIGS. 3A and 3B show glucometer values in mg/dL on the vertical axis and the horizontal axis is in detector voltage values using a bolometric detector. FIG. 3A is a single day's data and FIG. 3B is a combination of multiple days' readings calibrated to a set standard value.

FIG. 4 is an image of an eye using an MIR camera. Spectral selection was due to camera response max centered on 10 micron region. The dark ring around the eye was used as a reference. The small dots seen in the image are measurement points were pixel values are obtain in three colors. The total value corresponds to the MIR energy emitted per pixel.

Figure 5A:
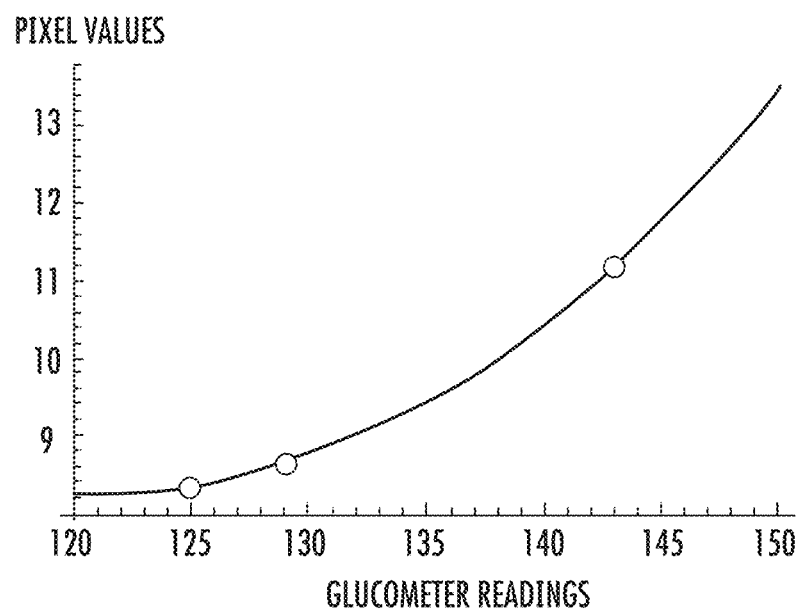
FIGS. 5A and 5B are graphs showing MIR pixel values as a function of glucose concentration (mg/dl) from a glucometer for a diabetic (FIG. 5A) and non-diabetic (FIG. 5B).
Figure 5B:
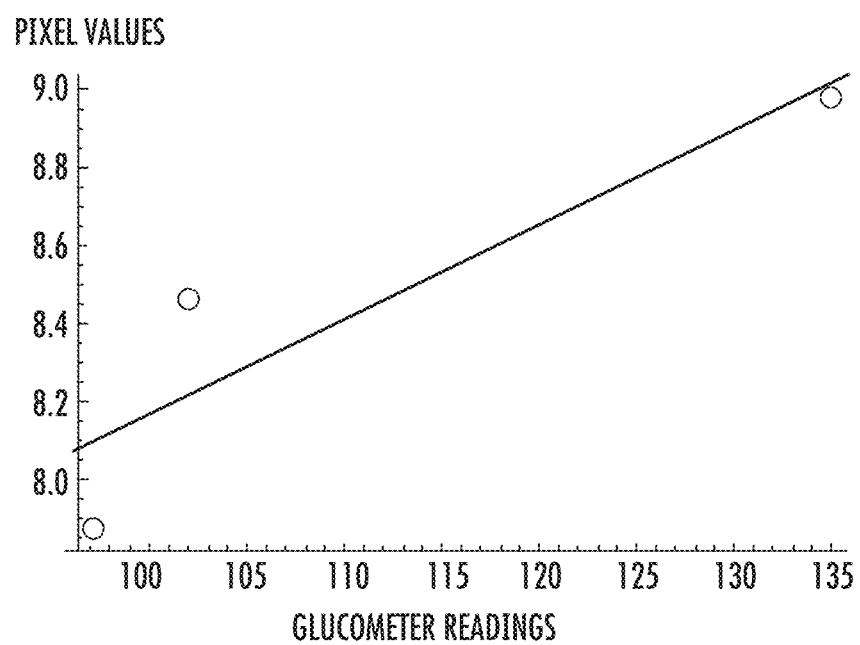

The averages over the eye values were normalized to the reference ring. FIGS. 5A and 5B are plots of MIR grayscale pixel values versus glucometer readings for a diabetic (FIG. 5A) and non-diabetic (FIG. 5B). Not only was there a strong correlation between grayscale pixel values and glucometer readings but also the sensitivity is sufficient such that one can distinguish between readings of 125 and 129 mg/dL (FIG. 5A). FIGS. 5A and 5B utilize a pixel value scale related to photon counts that the sensor of a sensor reads. These are correlated with the radiance or temperature via algorithms programmed via computer readable memory and a corresponding processor in the apparatus, e.g., pixel values based on grayscale intensity in terms of photon counts or energy. The gray scale images remove Red Green Blue color value effects. It is these grayscale values, which may be expressed as multi-bit intensity values, indexed intensity values, or on a logarithmic scale for photon emissions, that are then matched to radiance and temperature correlations via software stored in the apparatus described herein.

As shown in FIG. 5B, a strong correlation exists between grayscale pixel values and glucometer readings as before. Again sensitivity is good, i.e. 97 and 102 mg/dL are easily distinguished.

Therefore, there is a strong correlation between MIR values measured in eye fluid films and blood glucose levels. This opens the door to a new class of medical devices that can be effectively used in diabetic self-monitoring.

Example 2

Figure 7:
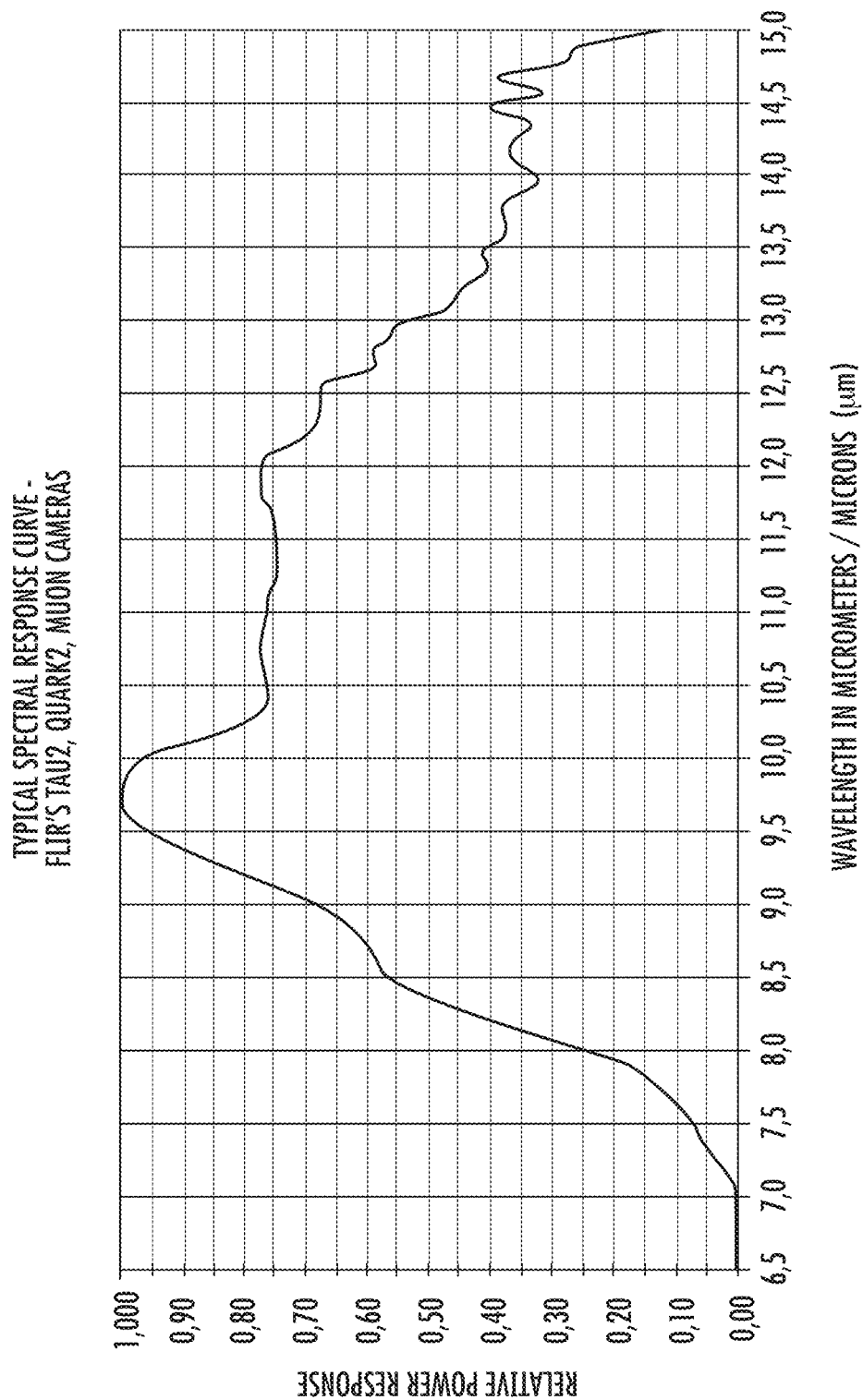
FIG. 7 is a plot of the sensor responses in the MIR range of a FLIR sensor (FLIR Systems, Inc.). The key feature is that the maximum sensor response occurs in the 9 to 10.5 micron range.

FIG. 7 is a plot of sensor responses in the MIR range provided by an example manufacturer (i.e., FLIR Systems, Inc.). The key feature is that the maximum sensor response occurs in the 9 to 10.5 micron range. It should be understood that, although this is FLIR camera data, the bolometer has a similar response.

Figure 8:
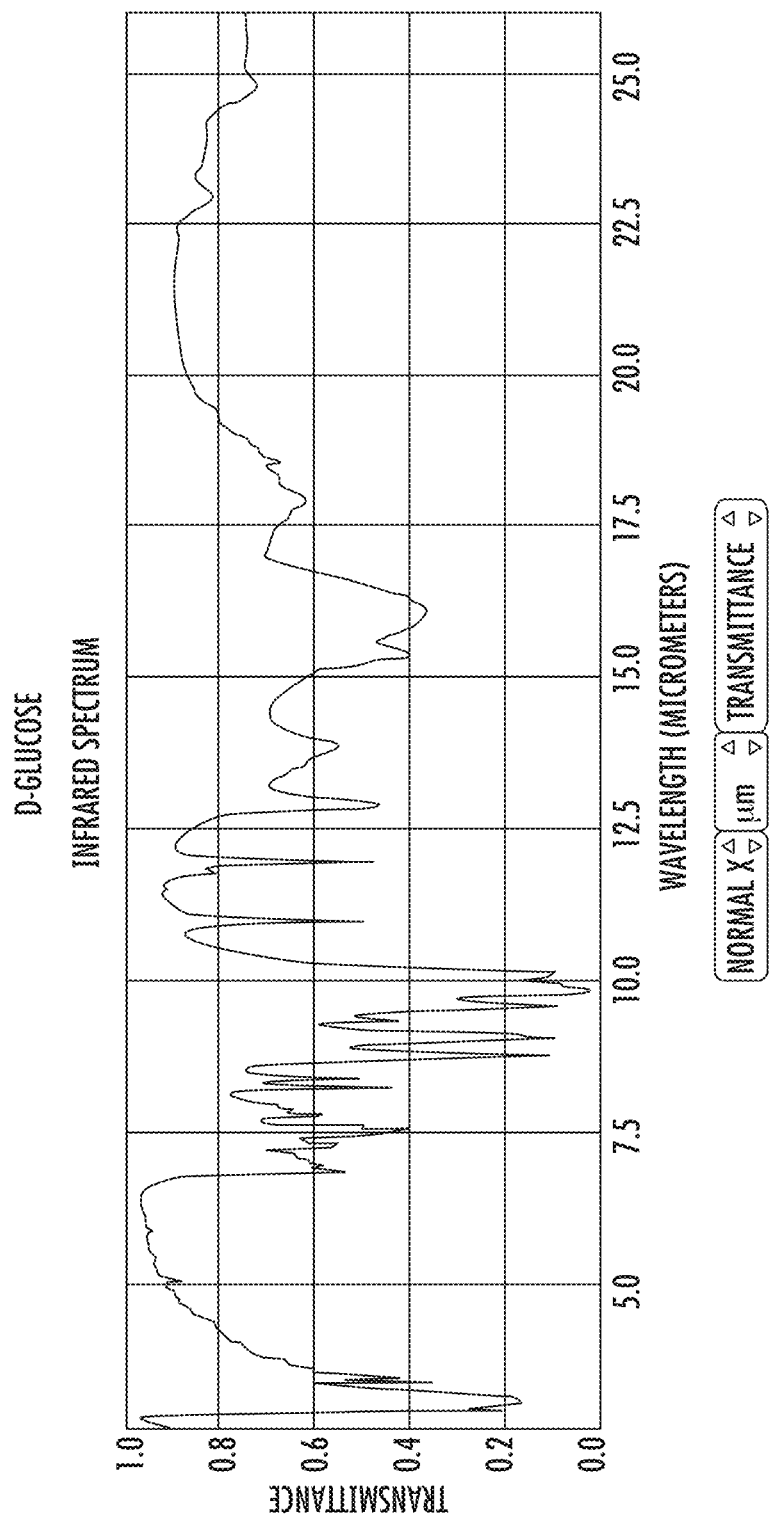
FIG. 8 shows the transmittance of glucose over the MIR range (National Institute of Standards and Technology—NIST). Glucose transmits the least amount of radiation in the 9 to 10 micron range.

FIG. 8 shows the transmittance of glucose over the MIR range (figure obtained from the National Institute of Standards and Technology—NIST). Glucose transmits the least amount of radiation in the 9 to 10 micron range. This curve is an excellent approximation to a glucose and water solution.

Figure 9:
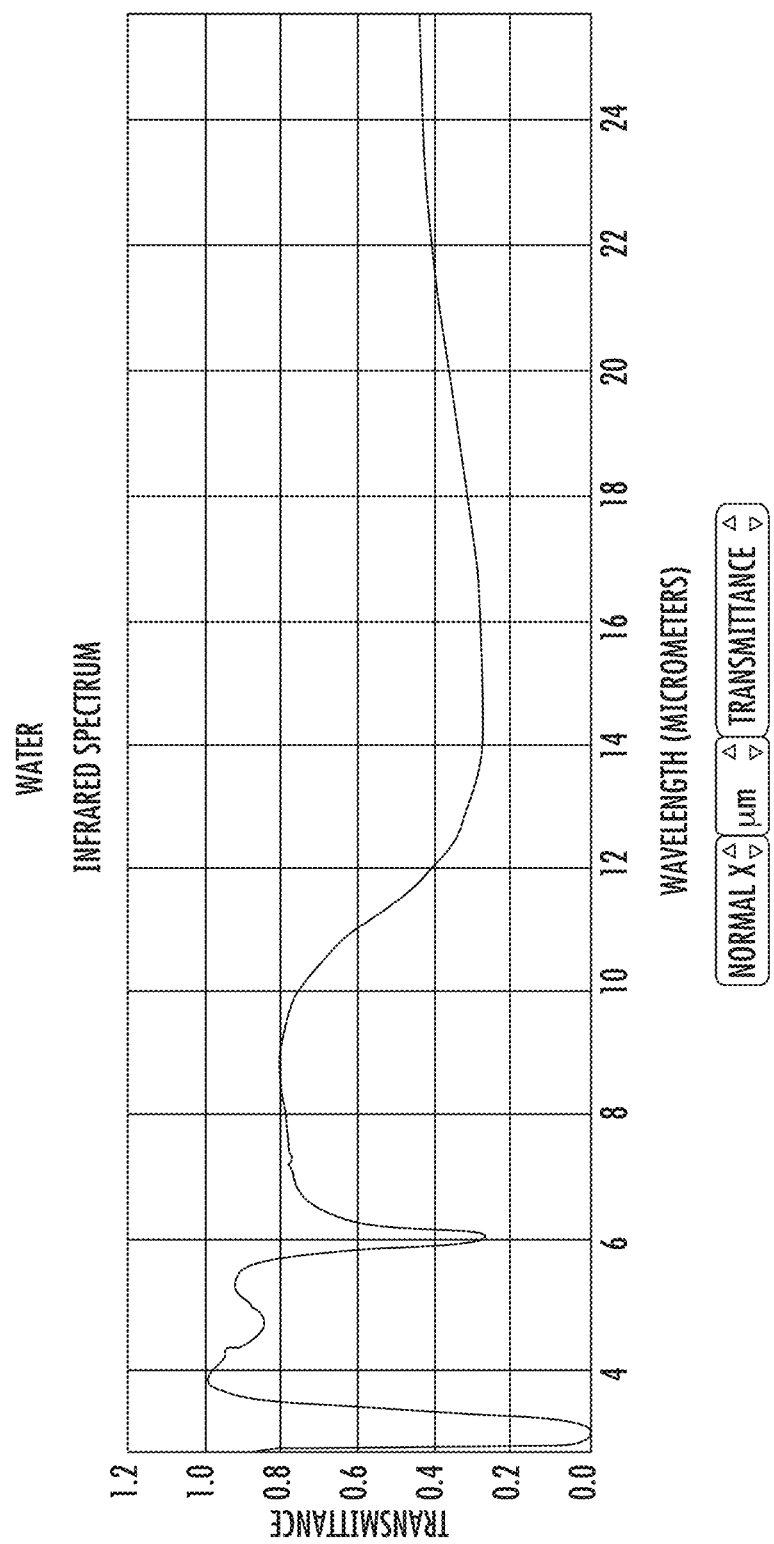
FIG. 9 shows the transmittance of water over the MIR range (NIST database). It transmits about 80% of the radiation in the 9 to 10 micron range

FIG. 9 shows the transmittance of water over the MIR range (NIST database). It transmits about 80% of the radiation in the 9 to 10 micron range.

From the plots shown in FIGS. 7-9, it can be seen that these detectors, combined with the transmittance of glucose and water, indicate that the maximum effect of a glucose solution in the eye fluid would occur in the spectral range where the sensors sensitivity is optimized. i.e. 9 to 10 microns.

This is the best spectral range to detect glucose. This work is summarized in a study of the application of Fourier Transform-IR Spectroscopy. In clinical examples for the control groups of FIGS. 10-12, a Fourier Transform analysis of infrared image pixel values (FT-IR) was conducted for attenuated total reflectance (ATR) data gathered for control solutions. While in vivo testing of a subject's eye measures mid-range infrared emissions from an eyeball, without directed infrared radiation from the camera to the eye, the ATR analysis of the control samples utilizes the ATR method of directing infrared radiation at the sample and measuring reflected radiation back onto the sensor. For FIGS. 10-12, ATR FT-IR Spectroscopy was used to measure the concentration of glucose in aqueous samples including ones mixed with artificial tears to mimic the composition of the intraocular fluid. The vibrational modes of glucose in the region, 980-1200 $cm^{-1}$, were exploited as identifiers of the concentration of the glucose. The transmission, at the two peaks (1030 $cm^{-1}$ and 1078 $cm^{-1}$) chosen for analysis, is proportional to the concentration of the glucose in the sample. At concentrations above 90 mg/dL this method appears to be a valid technique to measure the concentration of glucose in aqueous solutions with a sensitivity of 20 mg/dL.

Figure 10:
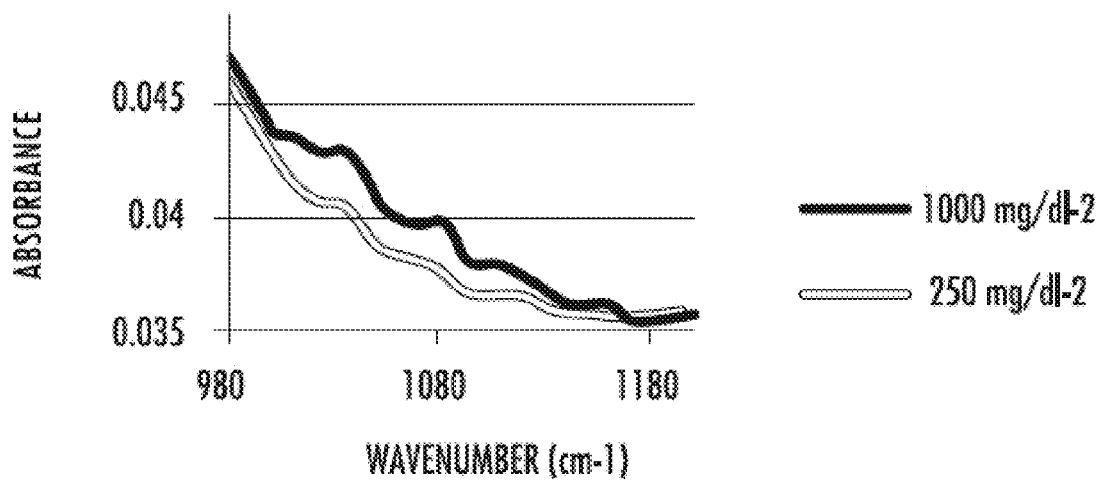
FIG. 10 is a plot of absorbance as a function of wavenumber for two varying concentrations of glucose in aqueous solution. The spectrum was taken with the Varian 640-IR FT-IR spectrometer. In the region of interest there are two peaks for glucose 1030 cm$^{-1}$ and 1078 cm$^{-1}$ (9.7 and 9.3 microns (μm), respectively).
Figure 11:
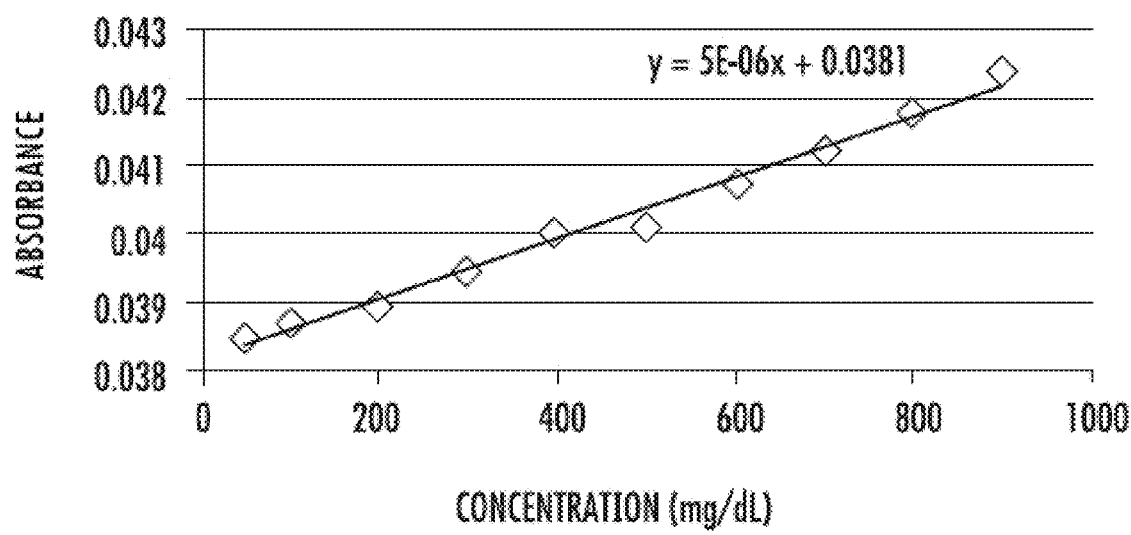
FIG. 11 is a plot of the absorbance peak at 1030 cm$^{-1}$, 9.7 microns (μm) for various concentrations of glucose. The FTIR transmission at this wavenumber is related to the concentration.
Figure 12:
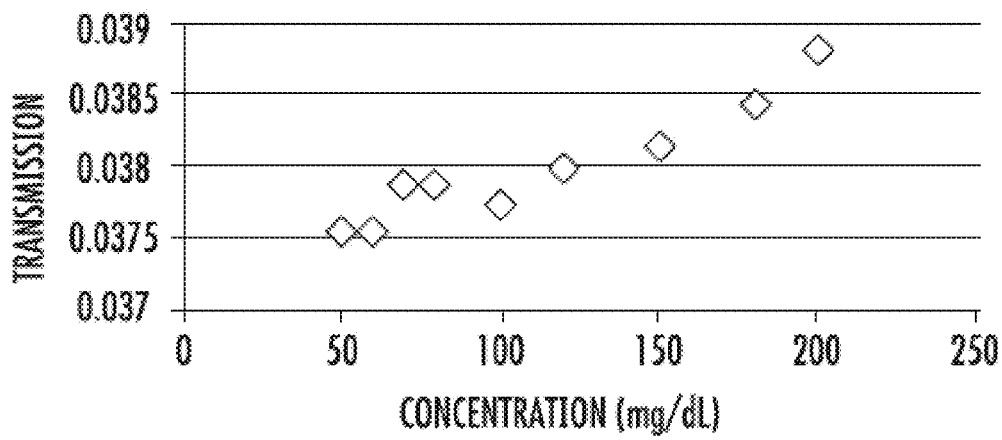
FIG. 12 is a plot of the absorbance peak at 1030 cm$^{-1}$, 9.7 microns (μm) for glucose concentrations that would be most frequently found for a controlled diabetic.

As seen in FIGS. 10-12, the transmission value (and the associated absorbance) varies for the glucose peaks at various concentrations of water. This is true for control specimens having glucose in both water and in water mixed with the artificial tears. When the absorbance is plotted as a function of concentration at higher concentrations (90-1000 mg/dL), there is a linear relationship which occurs regardless of the peak, 1030 or 1078 cm$^{-1}$, analyzed (see FIG. 10). At lower concentrations of glucose (50-90 mg/dL), however, the plot is no longer linear. The linear fit at the higher concentrations is reproducible. Differences of 20 mg/dL glucose concentrations are detectable using this method.

FIG. 10 shows the results of a control test that plots absorbance as a function of wavenumber for two varying concentrations of glucose in aqueous solution. The spectrum was taken with the Varian 640-IR FT-IR spectrometer. In the region of interest there are two peaks for glucose 1030 cm$^{-1}$ and 1078 cm$^{-1}$ (9.7 and 9.3 microns, respectively).

Various glucose concentration standards were created and the spectra were taken. FIG. 11 is a control plot of the various concentrations and the absorbance peak at the wavenumber of 1030 cm$^{-1}$ and wavelength at 9.7 microns. The FTIR transmission at this wavenumber is related to the concentration.

FIG. 12 is like FIG. 11 but concentrating on the lower glucose concentrations. This is the region where the glucose values would be most frequently found for a controlled diabetic.

The Bolometric Sensor

In the case of the Micro-Epsilon sensor, the device can be fixed in a mounting stand so the test subject can move their eye to approximately 2 cm from the sensor. There can be head and eye supports so that motion is limited. While looking directly at the sensor, lens and data can be collected for 2 seconds. This can generate 200 readings, which are then averaged automatically by the data acquisition system. Immediately after the eye reading a blackbody is placed before detector at the same position of the eye in the previous test and the measures are repeated to provide blackbody reference values. The difference between the bolometer eye values and the blackbody reference (BB) values, ΔV, is taken as "the data" for correlation with blood glucose values (BGVs). The averages are taken as ΔV/BB to be correlated to BGV.

The bolometric sensor is generally inexpensive. A medical monitoring device based on this class of sensor should be easy to develop. This type of sensor is also generally less sensitive than one similar to the full IR camera would be.

Figure 13:
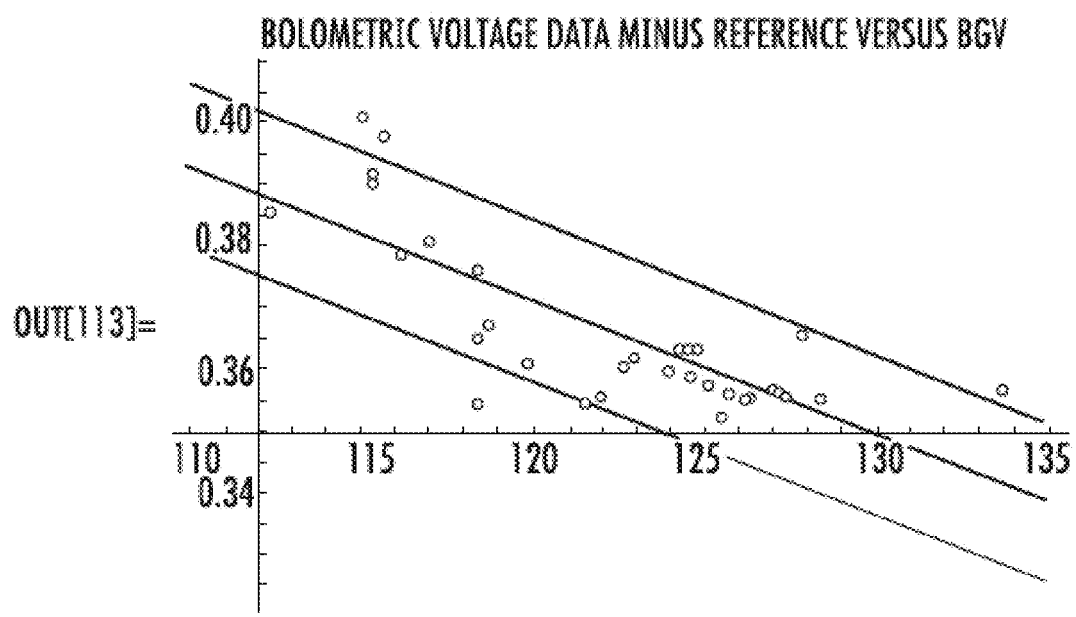
FIG. 13 shows bolometer voltage data ratios, taken with respect to a blackbody reference, with blood glucose values using a standard glucometer. There are 30 readings in this data set. The plot is linear as expected and decreases with increasing blood glucose value (BGV) since it is an absorbing film.

FIG. 13 relates bolometer voltage data ratios, taken with respect to a blackbody reference, with blood glucose values using a standard glucometer. There are 30 readings in this data set. Again the plot is linear as expected and decreases with increasing BGV since it is an absorbing film.

The data spread is primarily due to eye temperature. Otherwise there is random noise in the signal. The data in this plot has been noise filtered before presentation. The central line is the linear fit and the two side-lines represent plus/minus one standard deviation.

The FLIR Camera

The FLIR camera is more sensitive and provides radiance data as well as temperature values. For this reason, it was used for the basic feasibility studies.

Procedure:

First an infrared (IR) image of the eye can be made that is displayed in a multi-color format. Once again, the head and eye placement can be restricted by a head-rest and an optical iris. These maintain the same configuration each time. It is the radiance data that is the most valuable. The following shows how this data is isolated for specific eye regions.

An iris can be used to hold the relative position between the camera and the test subject's eye. It also can provide a reference for the temperature and radiance data field.

At the same time that this image is acquired the camera can produce a file of radiance and a temperature data per pixel that matches the color image.

These files can be presented as gray scale images. Since it is difficult to find regions in the eye from a gray scale radiance data image, the multi-colored image can be used to create a mask that localizes each area of interest within in the eye:

The areas of interest are in some cases the left and right corners and center of the eye. The highest eye temperatures are generally in the right corner (near the nose) followed by the left then the center. There is about a 2 degree C. variation between these values.

The mask and gray scale radiance image can then be multiplied together to form another image of radiance data isolated within the areas of interest.

The radiance data can then be averaged over each region to provide information such as:

{127, 0.00428962, 0.00428217, 0.004344389}

127 is a BGV added for the purpose of illustration and 0.00428962 is in Watts/cm2-strd.

Using this same procedure a temperature value, degrees C. below, can be obtained for each area:

{127, 0.00428962, 0.00428217, 0.00434438, 33.6500, 33.3320, 34.3795}

Figure 14:
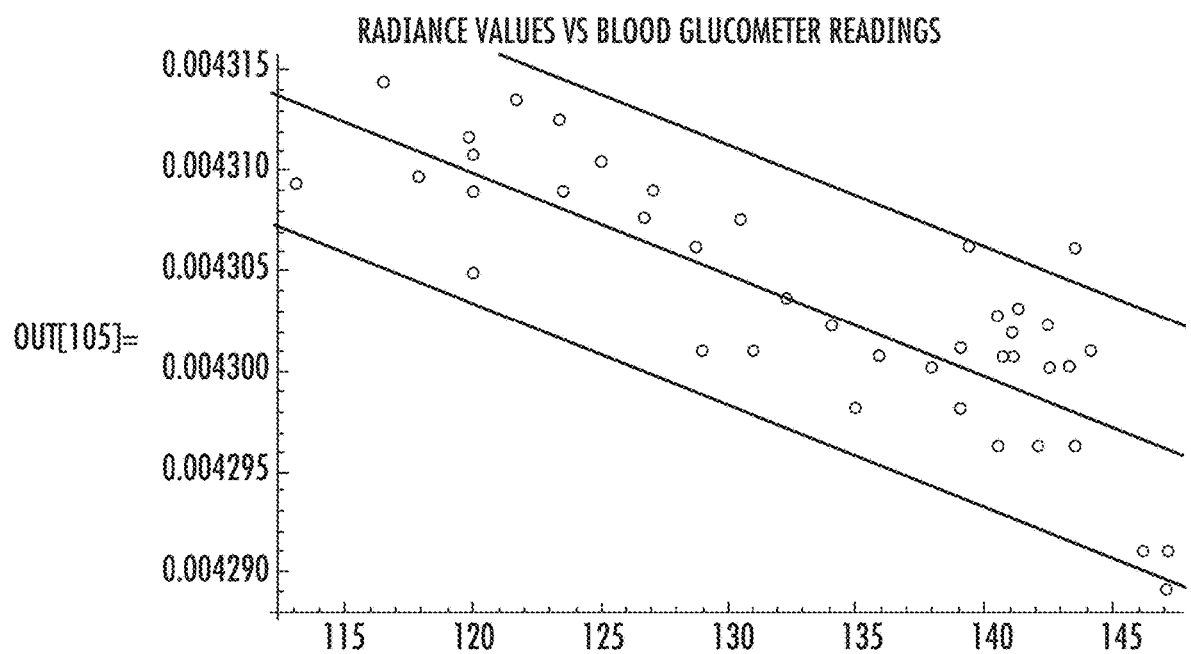
FIG. 14 relates radiance data with blood glucose values using the FLIR camera data. There are 45 readings in this data set. The plot is linear as expected and decreases with increasing BGV since it is an absorbing film.
Figure 15:
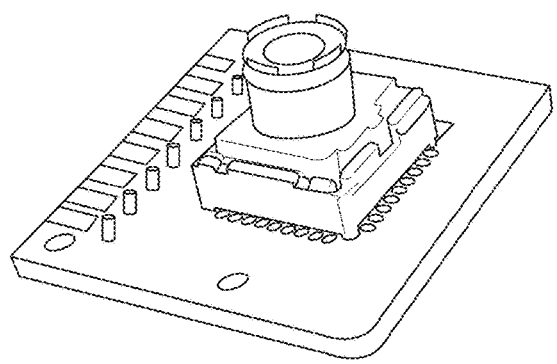
FIG. 15 shows an example MIR camera for use in the disclosed optical glucometer.
Figure 16:
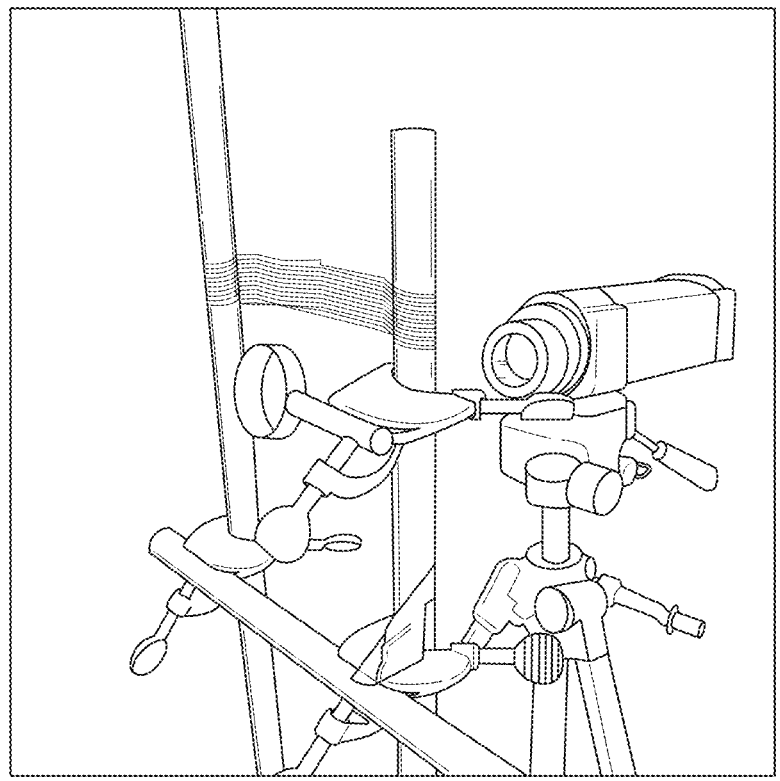
FIG. 16 shows an example optical glucometer with an FLIR camera mounted with a head support and iris.

Results:

FIG. 14 relates radiance data with blood glucose values using the FLIR camera data. There are 45 readings in this data set. The plot is linear as expected and decreases with increasing BGV since it is an absorbing film.

The data spread is primarily due to eye temperature. Otherwise there is random noise in the signal. The data in this plot has been noise filtered before presentation. The central line is the linear fit and the two side-lines represent plus/minus one standard deviation.

Since there are temperature variations within the eye and between testing sessions, models were developed that can be used to make adjustments for these variations. These are based on ideal blackbodies, the camera response and water attenuation of the signal. These would be part of system's data analyses software.

Another issue is day to day tracking of readings. This is addressed by referencing all readings to a standard, i.e. blackbody values or control glucose solutions.

Embodiments of an optical glucometer as disclosed herein may be considered in terms of methods and apparatuses using the correlation between MRI induced voltages and blood glucose values as previously described. The physical correlation between optical glucose concentrations and voltage responses in the disclosed hardware for a bolometer allow for methods and apparatuses that conveniently provide blood glucose values for a subject. In another example, the physical correlation between radiance emissions from a subject's eye and an associated thermal image analysis, taken at a given wave number, provides similar blood glucose evaluation.

Considering a bolometer embodiment first, in one embodiment, a bolometer may be used to perform a method of determining blood glucose concentration in optical fluid, e.g., tears forming fluid films on an eyeball surface. The method incorporates measuring a subject's (human or other animal) blood glucose concentration by measuring the glucose concentration in the tears on the eyeball. These measurements occur in vivo with real time data analysis.

The method of measuring blood glucose concentration in a fluid film on an eyeball of a subject includes having a set of standard control values for known glucose concentrations in place, such as control values determined by the control test results of FIGS. 2A-2D and FIGS. 3A and 3B. Tabulating a set of standard control values for known glucose concentrations may include determining and storing a respective average of control voltage values induced at pixels of a mid-infrared radiation (MIR) sensor for MIR emitted through respective transmission media having known glucose concentrations. The method incorporates the use of a pixel by pixel analysis of voltages induced at each respective pixel by MIR incident on an array of pixels in a bolometer. In one aspect, a measurement cycle for blood glucose concentration includes collecting all necessary voltage measurements at each relevant pixel in an array of MIR sensitive pixels and storing, during the measurement cycle, voltage measurements corresponding to each voltage induced by mid-infrared radiation (MIR) emitted from the eye and incident upon the relevant pixels. One goal of the method is to identify a highly accurate average voltage measurement that can be correlated to control voltages, such as those set forth in FIGS. 2A-3B, and determine a subject's glucose concentration in the eye fluid. In one non-limiting analysis, the bolometer processes several measurement cycles, and for each measurement cycle, includes integrating the set of voltage measurements collected at each pixel in the sensor array to produce a single voltage value for the respective measurement cycle. Using a single voltage measurement determined from the array of pixels for each measurement cycle, the method includes calculating an average voltage measurement of the single voltage measurements across a plurality of measurement cycles. The average voltage measurement can then be used to determine a corresponding blood glucose concentration by selecting a known blood glucose concentration having a control voltage value equal to the average voltage measurement. The blackbody reference voltages induced as shown in FIG. 4 provide the necessary scaling for accuracy purposes.

In one embodiment, the bolometer is configured to induce voltages at pixels in a sensor having an array of pixels such that the voltages are induced for MIR having a wavelength of about 8 to 11 microns. Another embodiment includes inducing voltage at the pixels for MIR incident upon the pixels having a wavelength of about 10 microns. These wavelength determinations can be accomplished by either a lens configuration in the bolometer directing the MIR of particular wavelength to the array of pixels or in the materials used to form the pixels such that voltages are induced for particularly selected wavelengths. Accordingly, the wavelength of MIR directed to a sensor may be tuned to the proper wavelength for glucose analysis as set forth in the above discussions.

The method noted above may be implemented in an optical glucometer having a mid-infrared (MIR) sensor comprising an array of pixels connected to a processor that correlates blood glucose values to voltage readings induced by MIR incident upon the respective pixels. A computer memory is connected to the processor, the computer memory storing a set of the control values described above as including a respective average of control voltage values induced at the pixels for MIR emitted through known glucose concentrations. The glucometer is configured such that the control values are accessible by the processor. In one non-limiting example of data analysis, the processor may be configured with computer implemented instructions, or software, stored in computer readable media such that the processor receives, in a single measurement cycle, voltage measurements corresponding to each voltage induced by MIR incident upon respective pixels in an array of pixels. The processor integrates the voltage measurements and produces a single voltage value for the measurement cycle. With this single voltage measurement for multiple measurement cycles, the processor has sufficient data to calculate an average voltage measurement from the single voltage values corresponding to respective measurement cycles in a plurality of measurement cycles. The processor then correlates the average voltage measurement to a known glucose concentration stored in the memory by selecting a known glucose concentration having a control voltage value equal to the average voltage measurement.

In a different embodiment, the method of determining blood glucose concentration by analyzing optical fluid over a subject's eye may be implemented using a thermal image from an infrared camera. An infrared camera also has a pixel array connected to a processor that correlates blood glucose values to radiance measurements induced by mid-infrared radiation (MIR) incident upon the respective pixels. The processor and pixel array are connected to computer memory storing a set of standard control values. The standard control values include average control radiance values, for a selected wavenumber, induced at the pixels from MIR emitted through respective transmission media having known glucose concentrations. The control values are accessible by the processor to correlate an average radiance measurement from a thermal image to a known glucose concentration that has the same radiance value under control conditions. The infrared camera is configured to create a thermal image of a subject's eye, or portion thereof, and receive at the processor a radiance measurement corresponding to MIR incident upon each of the respective pixels within the camera sensor array. The camera sensor may be tuned, via lenses or the materials of the sensor itself, to produce a thermal image at a particular wave number for a given measurement cycle. The camera is configured to repeat the measurements over several thermal images and calculates an average radiance measurement over a plurality of thermal images. The average radiance measurement is correlated to a known glucose concentration having a control radiance value equal to the average radiance measurement.

As shown in FIG. 10, glucose concentrations are most readily detected in thermal images from cameras at wave numbers of 1030 cm-1 or 1078 cm-1. Using one of these wave numbers in camera set up, the thermal images are adapted for implementing the method of correlating radiance measurements to control radiance values as described.

Embodiments of a glucometer as described herein may incorporate hardware and software that allows for a glucometer to gather the data points at the location of the subject's eye and transmit the data to a remote server for data processing and results. To implement this embodiment, the glucometer may be a handheld device that encompasses a transceiver for wireless communications across a network, such as the internet. The glucometer may also have physical dimensions providing an appropriate wave number for glucose analysis as set forth herein. In one embodiment, the glucometer incorporates a collimating ring that not only determines the distance of the sensor from the subject's eye, but also provides reference data in a collected image. The collimating ring may be made of a material with an emissivity of about 1. In one example, the temperature of the collimating ring is held to a range of about 33 degrees Celsius to about 35 degrees Celsius, more particularly either 33 degrees Celsius or 34 degrees Celsius and resulting radiance values are used for calibration.

Example 3

In order to provide a system for patient self-monitoring, a more compact version of the system as compared to the system incorporating the FLIR camera (e.g., FLIR A325sc camera) is described below. Such a system can incorporate a relatively smaller thermographic imaging device such as the FLIR LEPTON camera to serve as the IR sensor and that can perform the same glucose detection as the FLIR camera.

The FLIR LEPTON camera has the same type of IR sensing chip, VOX micro-bolometer, that the more advanced FLIR A325sc uses but without cooling. Also, although it does deliver a red green blue (RBG) image, it is not supported by extensive analysis software within the camera. This disclosure contemplates that sensitivity could be improved, if needed, by cooling using a Peltier based devices. Also, a simplified data analysis system is needed to make interpretation of the readings. The necessary software for image acquisition and analyses, as well as a means to use this to make predictions of the patients BGV, have been developed as described below. The methodology and related devices revolve around the detection of the radiation and then the identification of the appropriate signals.

Data Acquisition

The following is the procedure for use of the FLIR A325sc camera to measure blood glucose, BGV, in the eye. The method is the same for a detection system based on the FLIR LEPTON camera as for a detection system based on the FLIR A325sc.

The patient looks directly into the camera at a distance of about 0.1 m while the camera records an image of eye and saves the image as CSV files. It should be understood that the data format (i.e., CSV file) is provided only as an example and that other data formats can be used. This process is repeated a plurality of times (e.g., 4 times) in rapid succession and the resulting data is averaged.

Figure 18A:
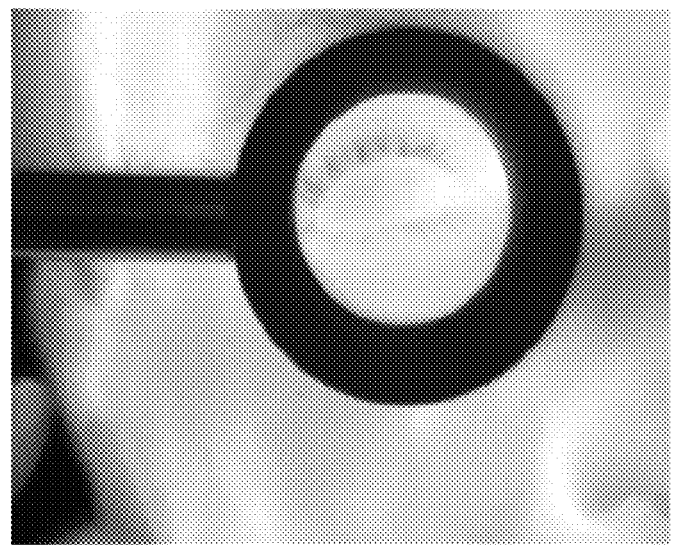
FIG. 18A shows an image generated using radiance data.
Figure 18B:
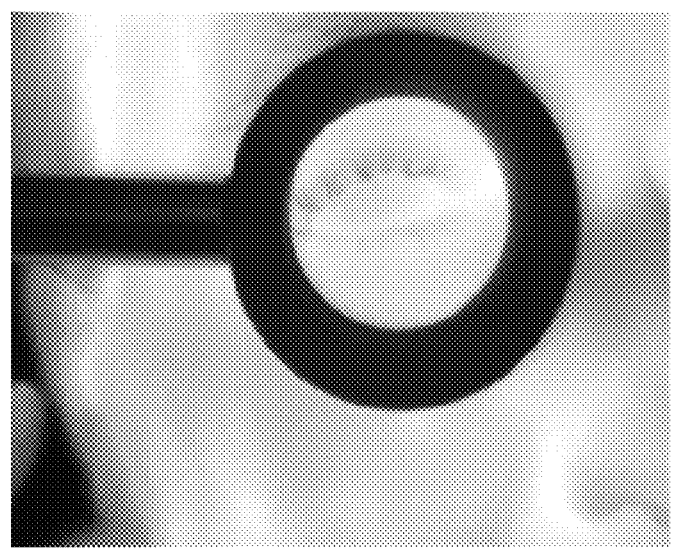
FIG. 18B shows an image generated using temperature data.
Figure 18C:
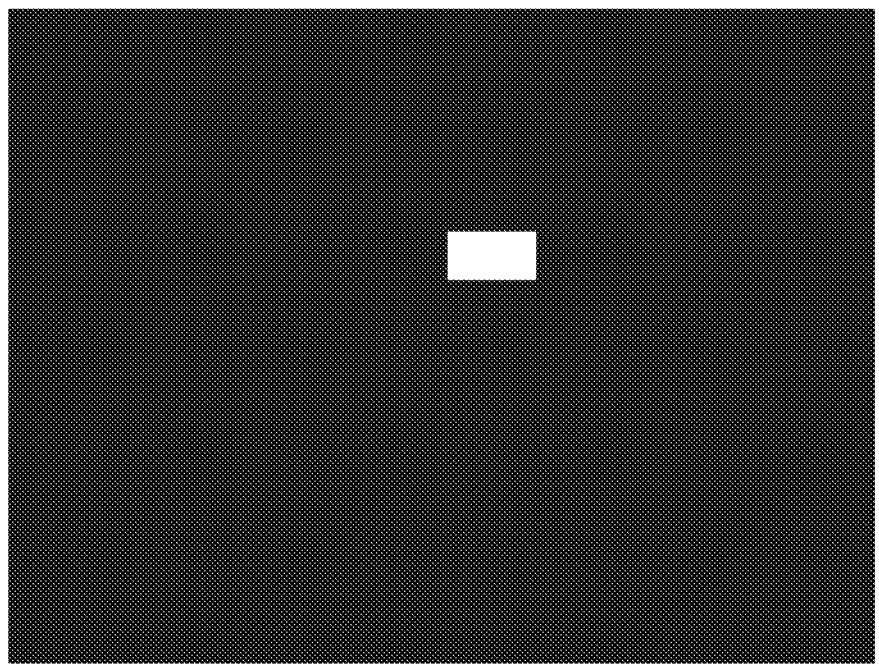
FIG. 18C shows a mask that can be used to define the pixel region of interest in each of the images.

Two sets of data are taken to allow for corrections due to temperature fluctuations. One of the CSV files has radiance data (Watts/cm$^2$-Sr) per pixel and the other file has temperature data ° C. These two files constitute the core of the data readings that are made to determine the glucose level in the eye. FIG. 18A shows an image generated using radiance data. FIG. 18B shows an image generated using temperature data. FIG. 18C shows a mask that can be used to define the pixel region of interest in each of the images. In FIG. 18C, the mask is rectangular in shape and corresponds to a central region of the eye. As described herein, the size, shape, and/or location of the mask is not limited to the example in FIG. 18C. The mask ensures that the same area is compared within the eye images whether they be radiance or temperature field data. The masked image is then cropped to remove the radiance/temperature data field of interest as shown below.

This cropped image is a {17.33} pixel value field, 561 elements, with typical data of the form:

{0.00430927, 0.00431093, 0.00430939, 0.00430872, 0.00430759, \0.00430621, 0.0043061, 0.0043072, 0.00430605, 0.00430715, 0.00430791, \0.0043081, 0.0043076, 0.00431006, 0.00431159, 0.00431252, 0.00431627, \0.00431841, 0.00432107, 0.00432293, 0.00432496, 0.00432592, \0.00432877, 0.00432923, 0.00433073, 0.00433161, 0.00433528, \0.00433538, 0.00433793, 0.00433763, 0.00434009, 0.0043405, 0.00434075}

The field average is 0.00431981 Watts/cm$^2$-Sr.

In the same manner, the average temperature field over this region is obtained, in this case it is 33.9346 C.

The data sets are composed of three numbers; one is the blood glucose value, (from direct glucometer blood measurements), the radiance, and the temperature of the eye. The data format is {BGV, Radiance, Temperature C}. In this case, the set is:

{157, 0.00431981, 33.9346}

It has been found that in general the eye temperature is nearly constant at roughly 33.5° C. Since the eye acts as a blackbody emitting through the eye fluid film, which is basically a filter, the glucose absorbs the radiation from the eye. The nearly constant temperature makes it possible for an observer to discern the values of the blood glucose in the eye film from the background radiation. When there are significant temperature variations (e.g., +/- one degree or more) between measurements it is necessary to perform a temperature scaling, or correction, TC, to the radiance values so that all the data matches 33.5° C.

The temperature correction method is based on a temperature dependent function. The temperature dependent function is device specific and can be developed for a particular thermographic imaging device by using a standard blackbody and direct measurements of the radiance from the black body cavity. This provides a correlation between actual black body temperature and the radiance emitted by the black body as recorded by the thermographic imaging device. This takes into consideration the wavelength dependent response of the detector that is used in the thermographic imaging device (e.g., a FLIR A 325sc or FLIR LEPTON camera). The region in which the camera is most sensitive, the 8 to 14 µm range, yields a radiance versus as a function of temperature that is linear. The function that is derived from the method outlined above is 71% of a theoretical blackbody emitting over the same region at the corresponding temperatures:

DatafitBB[$Tp$]=0.002139894400283821'+ 0.00006380427549443183' $Tp$

The correction is then given by:

RadianceTC=(Radiance Measured)* (DatafitBB[33.5]/DatafitBB[$T$measured].

For this data set the corrections lead to the data elements {157, 0.00429228, 33.5}, where the radiance value is 99.4% of its test value.

Following the procedure outlined above, larger data sets have been obtained and employed in the development of the analytical means for BGV detection. The data sets obtained by this experimental method is patient dependent and can be generalized by acquiring data from a very large group of people over an extended time frame. This work has indicated that models can be developed that can allow generation of a "training" data set that can be used in a detection system. These models are described further below.

IR Transmission Through Solutions

It has been shown that an aqueous solution of glucose does in fact strongly absorb radiation in the 8 to 14-micron spectral region and that the absorption increases as the glucose concentration increases. The transmission of radiation through the glucose rather than the absorption has been examined, since this best describes the filter effect.

Figure 19A:
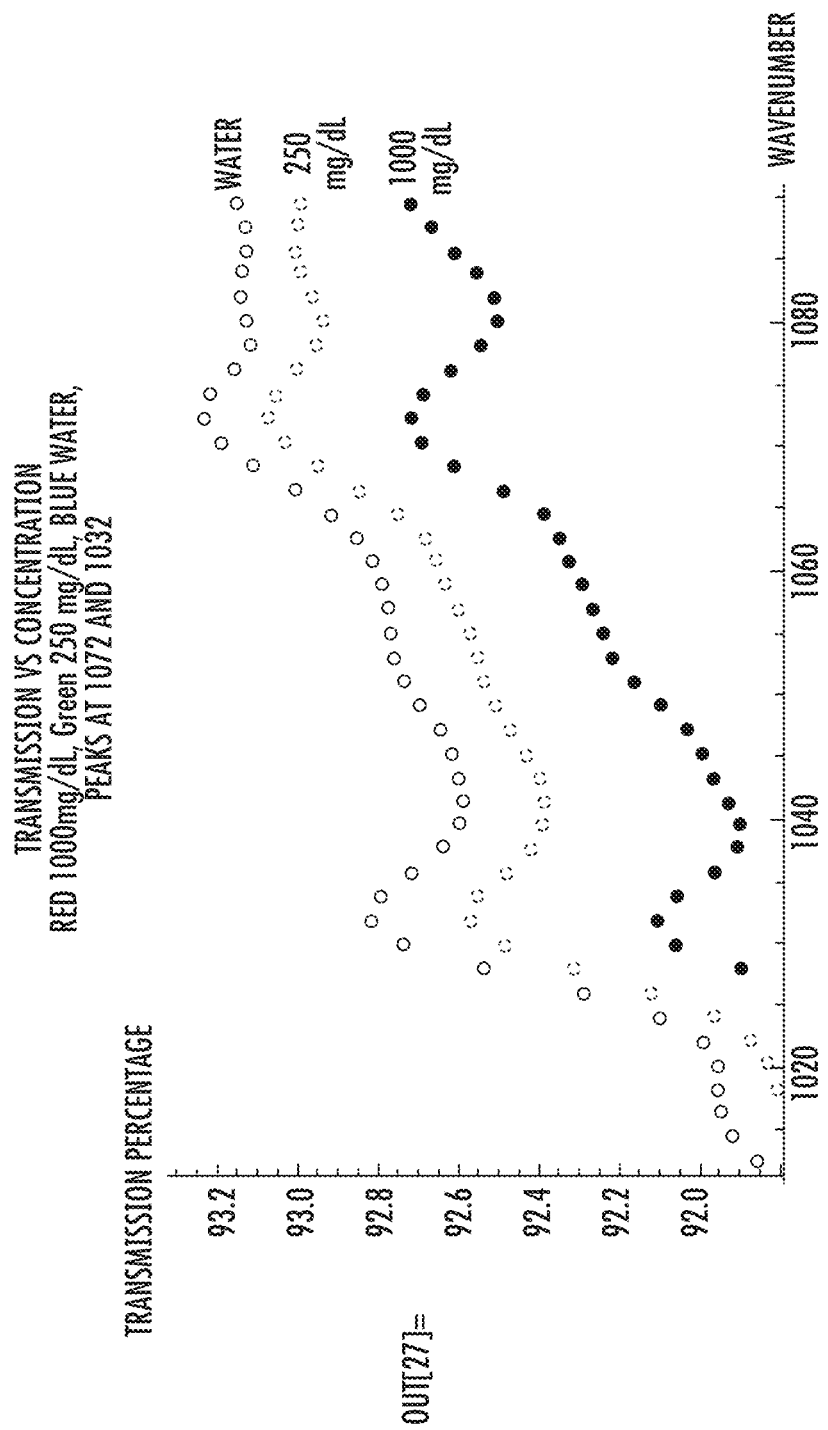
FIG. 19A illustrates three examples of transmission versus wavenumber over the primary region of interest, wavenumbers 1000 to 1100 $cm^{-1}$, where glucose absorption is most evident.
Figure 19B:
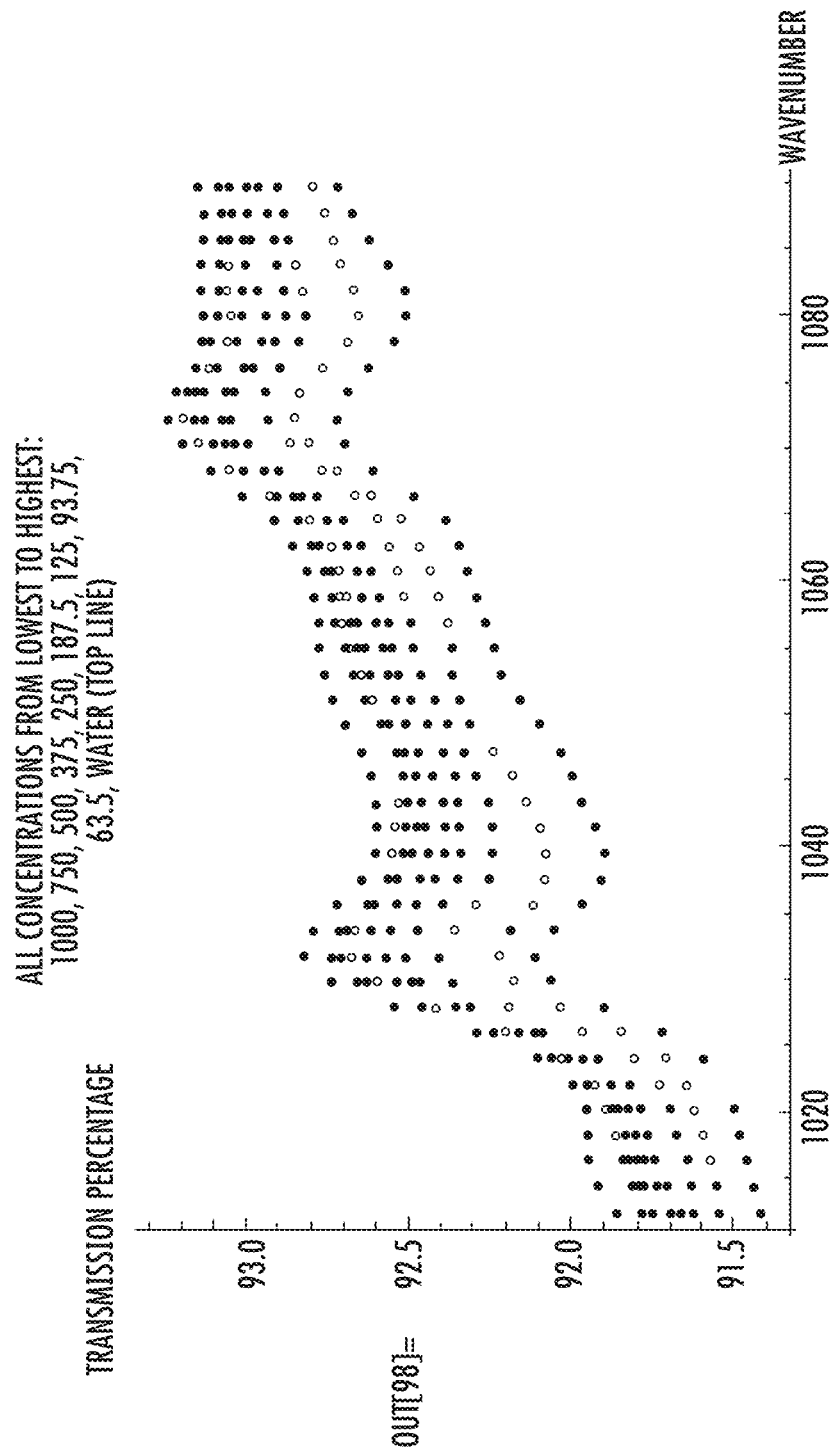
FIG. 19B illustrates a plot of all of the FTIR data. The 1000 mg/dl Concentration plot is the lowest line while water is the top most.
Figure 19C:
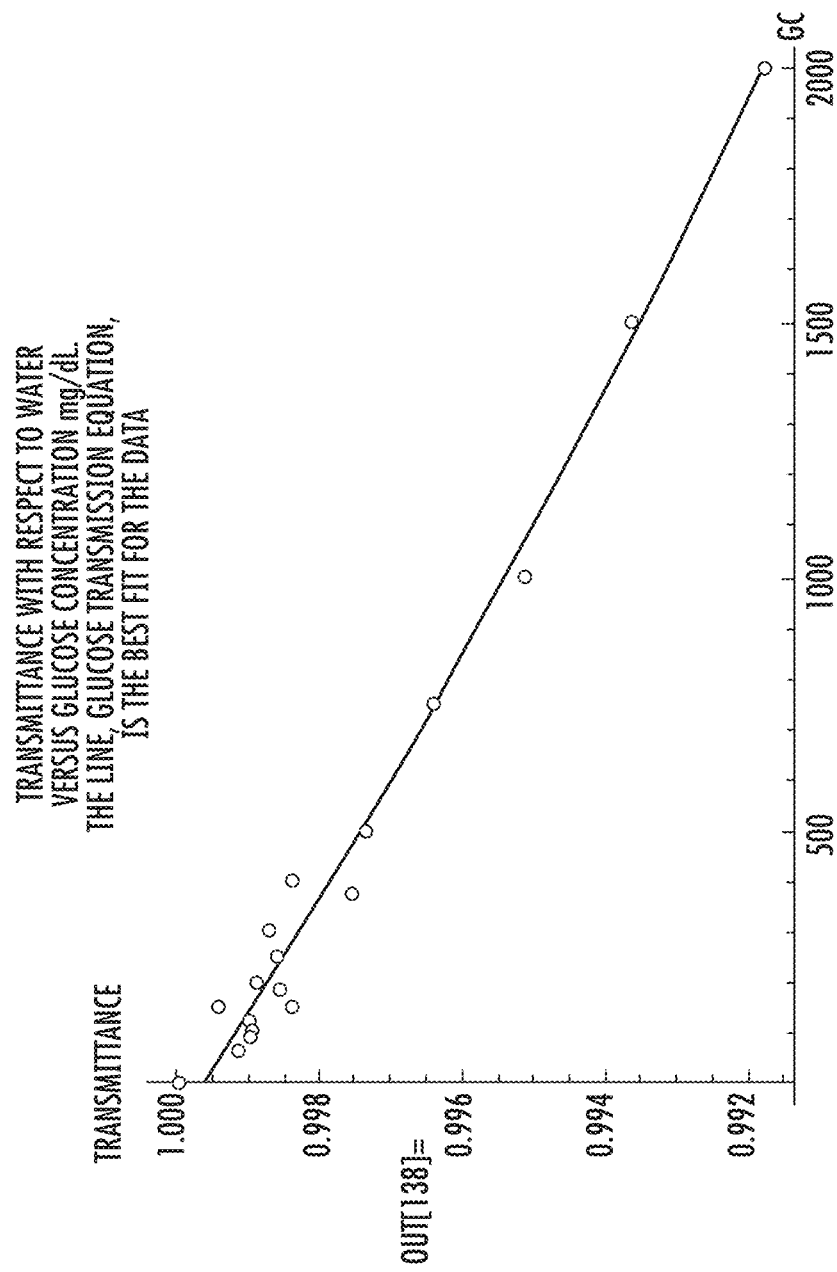
FIG. 19C illustrates the average areas under each curve, around the two peaks in the FTIR spectral data, with the variation in solution concentration.

The initial testing to confirm this was done by using a Fourier transform infrared spectrometer, Varian 640 FTIR. In these tests 10 µL solutions were placed in the spectrometer's ATR cell and the transmittance was measured across the spectrum for each solution. The concentrations range from roughly 50 to 2000 mg/dL. By using this extremely wide range and high values for concentration of glucose, it was possible to verify the trends in the data FIG. 19A illustrates three examples of transmission versus wavenumber over the primary region of interest, wavenumbers 1000 to 1100 cm$^{-1}$, where glucose absorption is most evident. FIG. 19B illustrates a plot of all of the FTIR data. The 1000 mg/dl Concentration plot is the lowest line while water is the top most. FIG. 19C illustrates the average areas under each curve, around the two peaks in the FTIR spectral data, with the variation in solution concentration. All of the solutions were run at room temperature so there were no other thermal effects. The same pattern is reveled if the concentration is plotted as function of the height of the peak. This disclosure contemplates that a Glucose Transmission Equation can be derived from the FTIR data of FIG. 19C. For example, the Glucose Transmission Equation can be a polynomial expression that follows from the FTIR data. This expression can be a best fit model to the FTIR data. This best fit model to the FTIR data is shown by the solid line in FIG. 19C.

Eye Model

Figure 20:
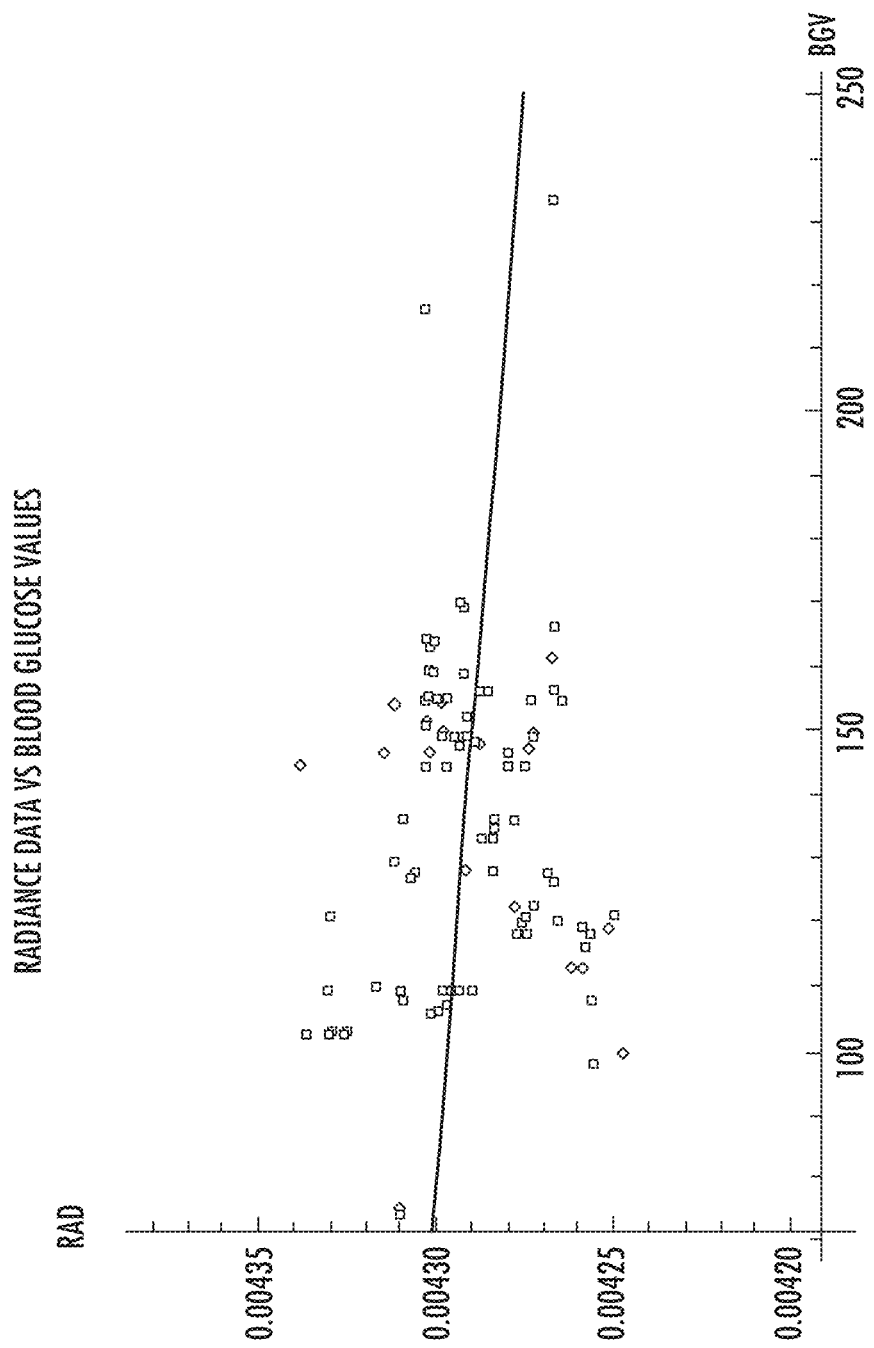
FIG. 20 illustrates a data set from an apparatus incorporating the FLIR A325sc camera consisting of 103 readings.

A system incorporating the FLIR A325sc camera has been used to generate a large data set for study. FIG. 20 illustrates a data set from a system incorporating the FLIR A325sc camera consisting of 103 readings. The correlation matrix for this is:

| 1 | −0.13055 |
|---|---|
| −0.13055 | 1 |

This is consistent with the negative correlations between radiance and BGV noted in the FTIR and surrogate eye studies.

The line in the plot is the best linear fit to the data and is its characteristic function:

CharacteristicFunct[BGV]=0.00431027914307337−
1.387389894556692×10$^{-7}$ BGV

For this data set the mean values are {132.675, 0.00429187, 33.5383} with the standard deviations {25.11, 0.0000266844, 0.370433}. Note that the average temperature is 33.5 C and that σ=0.0000266844.

Figure 21:
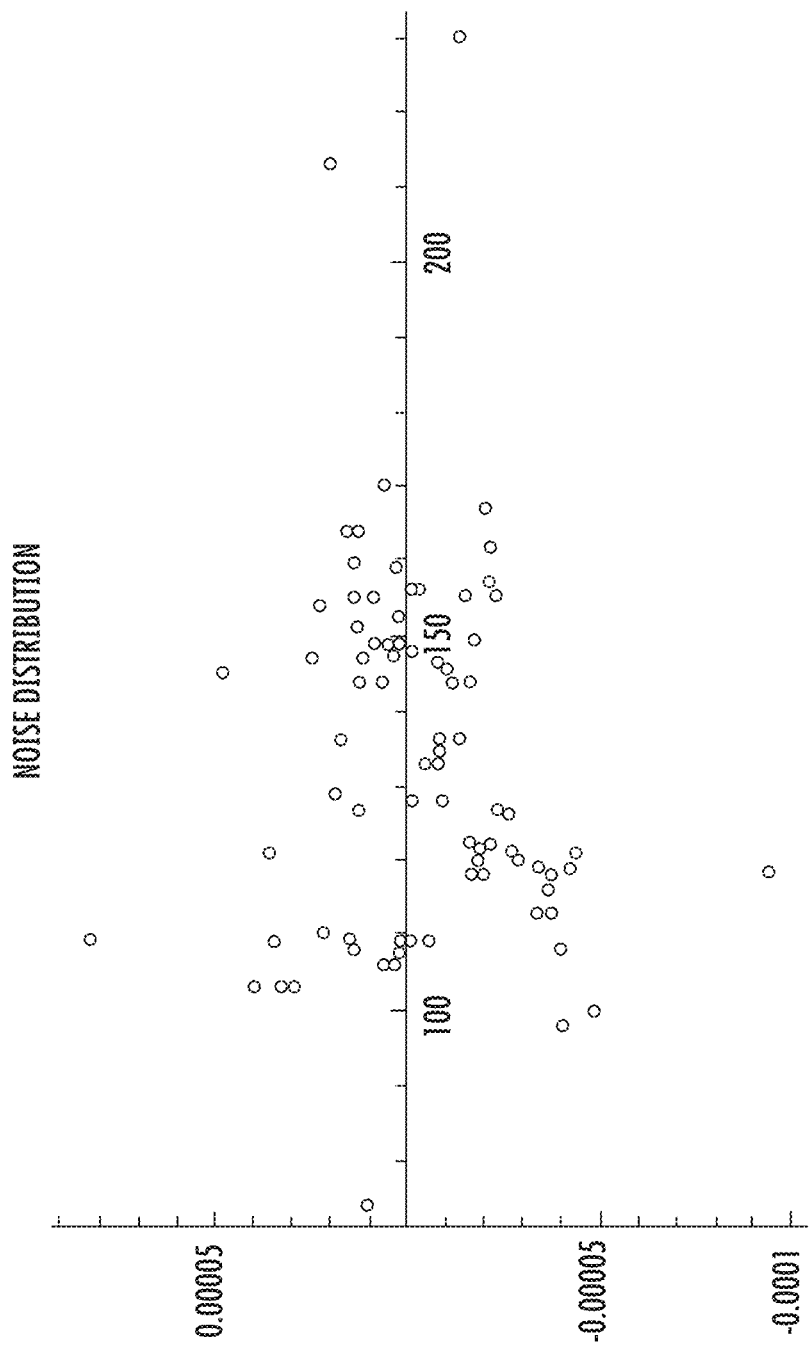
FIG. 21 illustrates a plot of noise distribution.
Figure 22:
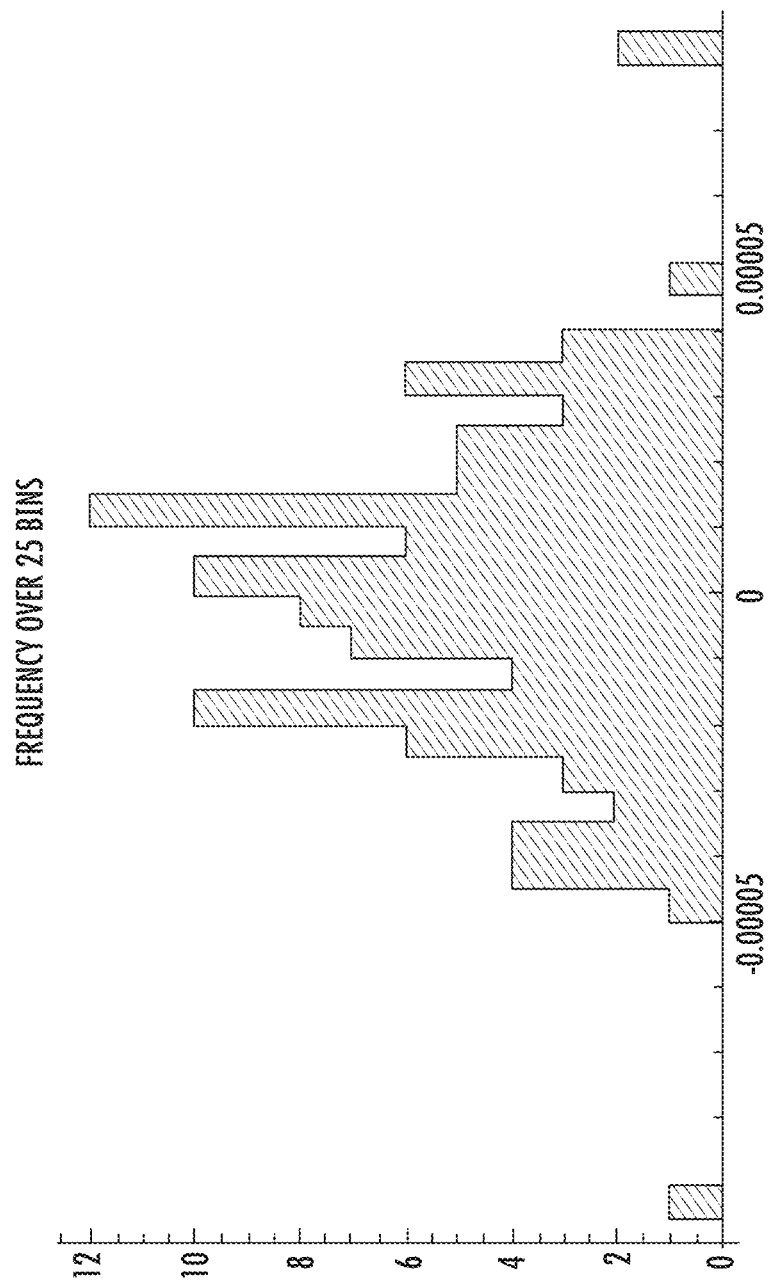
FIG. 22 illustrates the histogram of the noise.
Figure 23A:
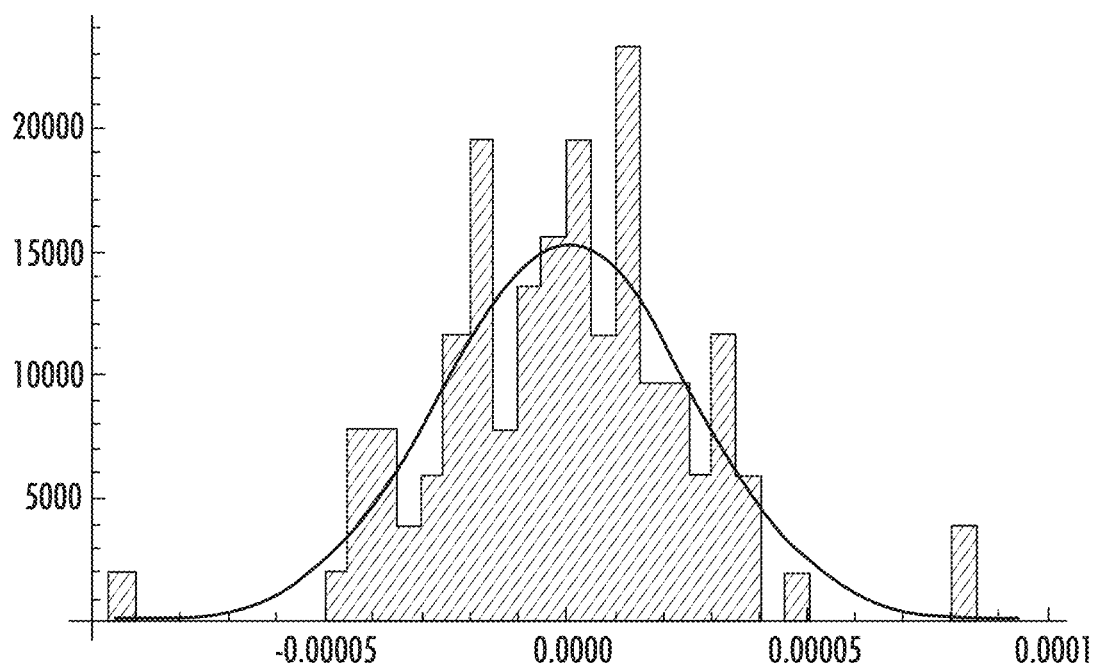
FIGS. 23A (probability density histogram and normal distribution data fit) and 23B (randomly generated data probability density histogram and normal distribution data fit) show that the noise is basically random which matches what is seen by the observations.
Figure 23B:
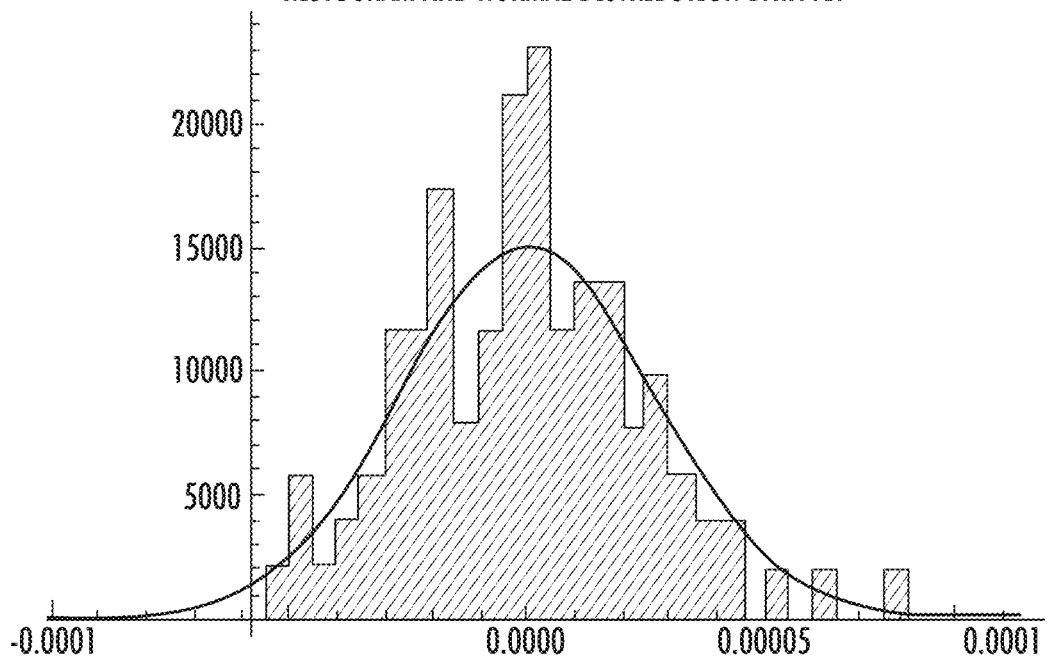

From the plot the scatter of the readings seems randomly distributed about the CharacteristicFunct line. This can be seen by subtracting the CharacteristicFunct values from the data set which produces a noise distribution as shown in FIG. 21. FIG. 22 illustrates the histogram of the noise. FIGS. 23A (probability density histogram and normal distribution data fit) and 23B (randomly generated data probability density histogram and normal distribution data fit) show that the noise is basically random which matches what is seen by the observations.

Having established randomness of the noise, it can be concluded that the average of many readings, perhaps 100, per evaluation session would decrease the scatter.

A theoretical expression for the CharacteristicFunct can be produced, which is designated as the EyeModel. This model is a function of BGV as has the functional form of:

(EyeModel[BGV]=NLAFunc[BGV]*(GlucoseTramsissionEquation[BGV]*DatafitBB[33.5]))

That is the Eye Model is equal to a nonlinear correction factor, NLA, multiplied by the product of the GlucoseTramsissionEquation and Black Body radiance at 33.5 C. As described above, the Glucose Transmission Equation can be derived from Fourier transform infrared spectrometer data.

Here the nonlinear correction factor expression is given by:

NLAFunc[BGV]=1.0080879109912388−
0.00002801460985031528*BGV

Figure 24:
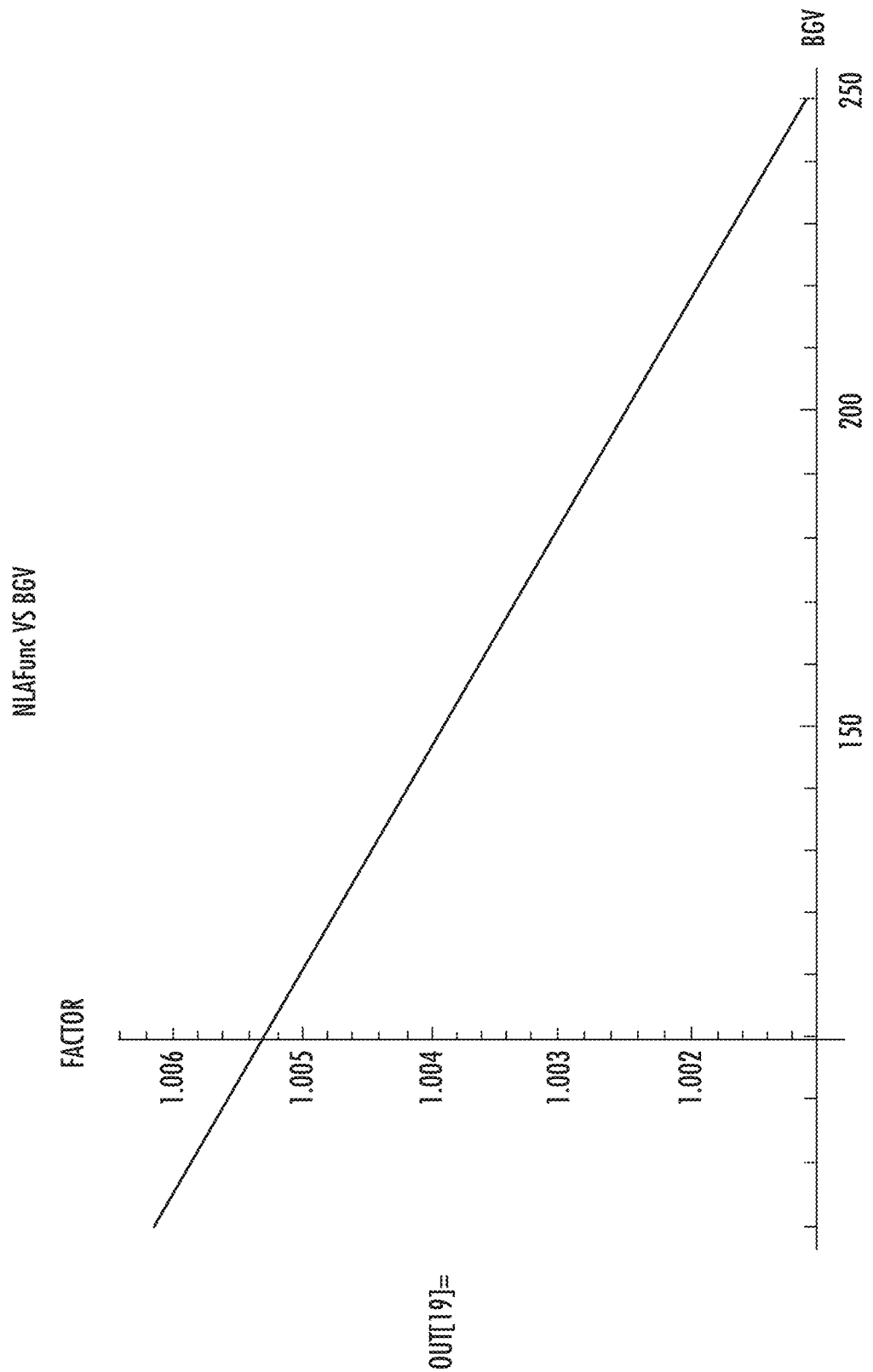
FIG. 24 illustrates the nonlinear correction factor (NLA-Func) as a function of BGV.

This nonlinear correction factor varies from 1.006 to 1.002, a dimensionless factor, over the BGV range of 70 to 250. So, this is a small correction as noted in the FIG. 24, which illustrates the nonlinear correction factor as a function of BGV.

Even though the nonlinear correction factor is nearly one for this data set, it is in general patient dependent and this represents the only point where patient uniqueness appears.

Figure 25:
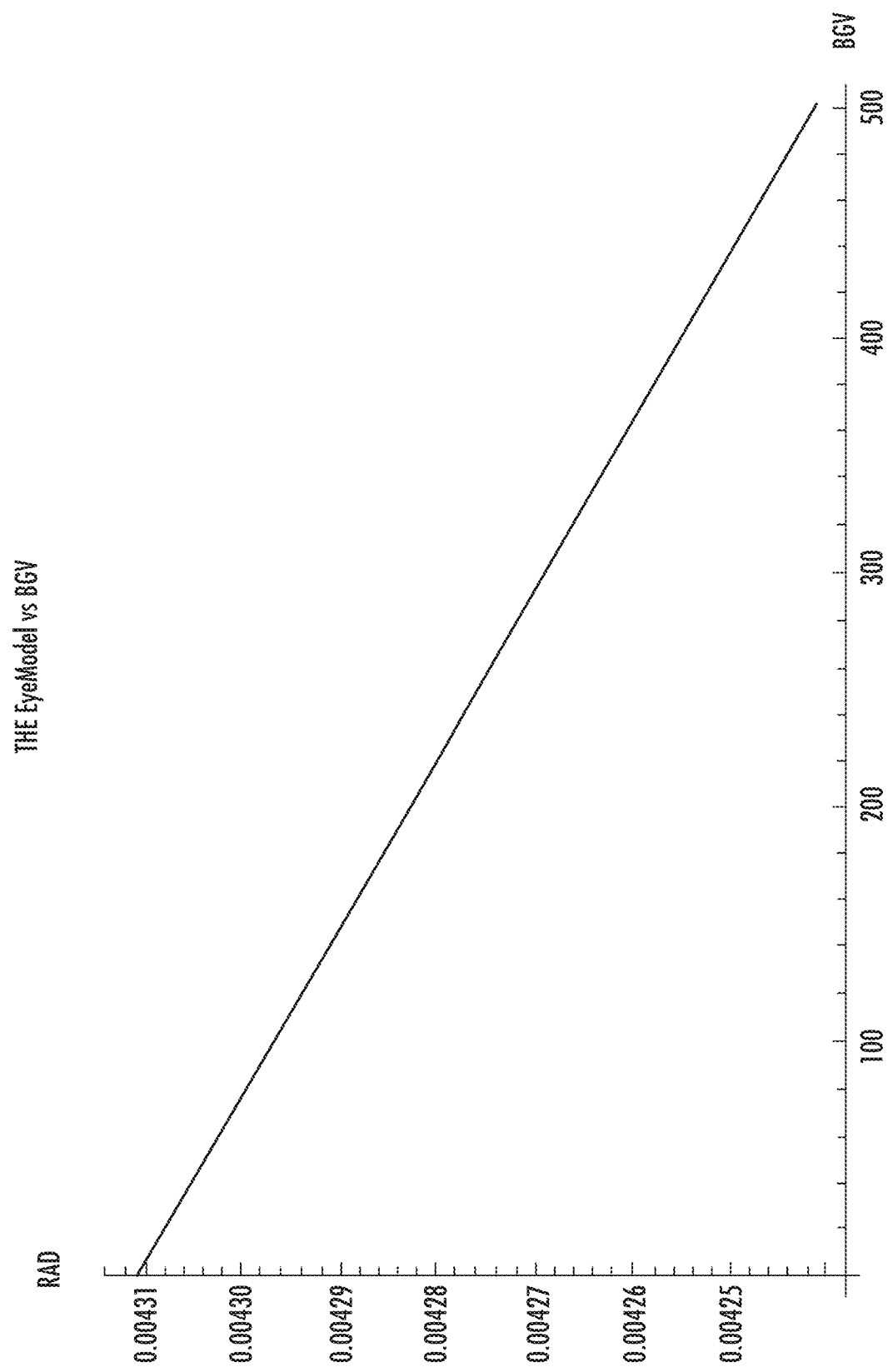
FIG. 25 illustrates radiance versus BGV according to the EyeModel for an extended range, without noise.

The end result for the EyeModel for an extended range, without noise, is shown in FIG. 25.

Predicting Blood Glucose Values from the EyeModel

The EyeModel fits exactly the CharacteristicFunct[BGV] without the noise field. To be a valid tool for BGV readings the noise does need to be included since any reading from a device will include it in the signal. The following plots summarize the findings to this point.

Figure 26:
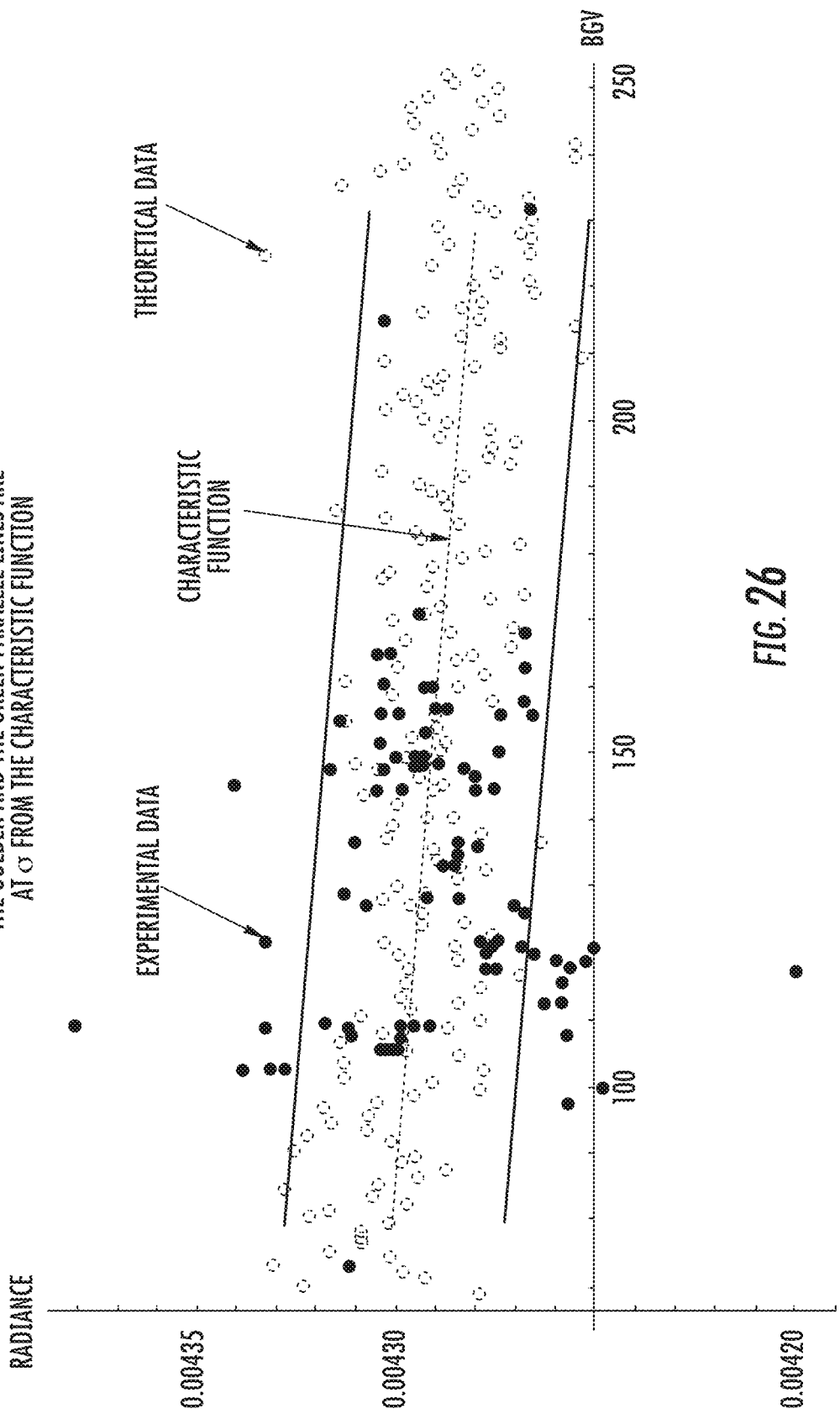
FIG. 26 shows experimental data, CharacteristicFunct and EyeModel with noise plots.

FIG. 26 shows experimental data. CharacteristicFunct and EyeModel with noise plots. The noise is represented by using a random normally distributed data field that is added to the EyeModel values.

Figure 27:
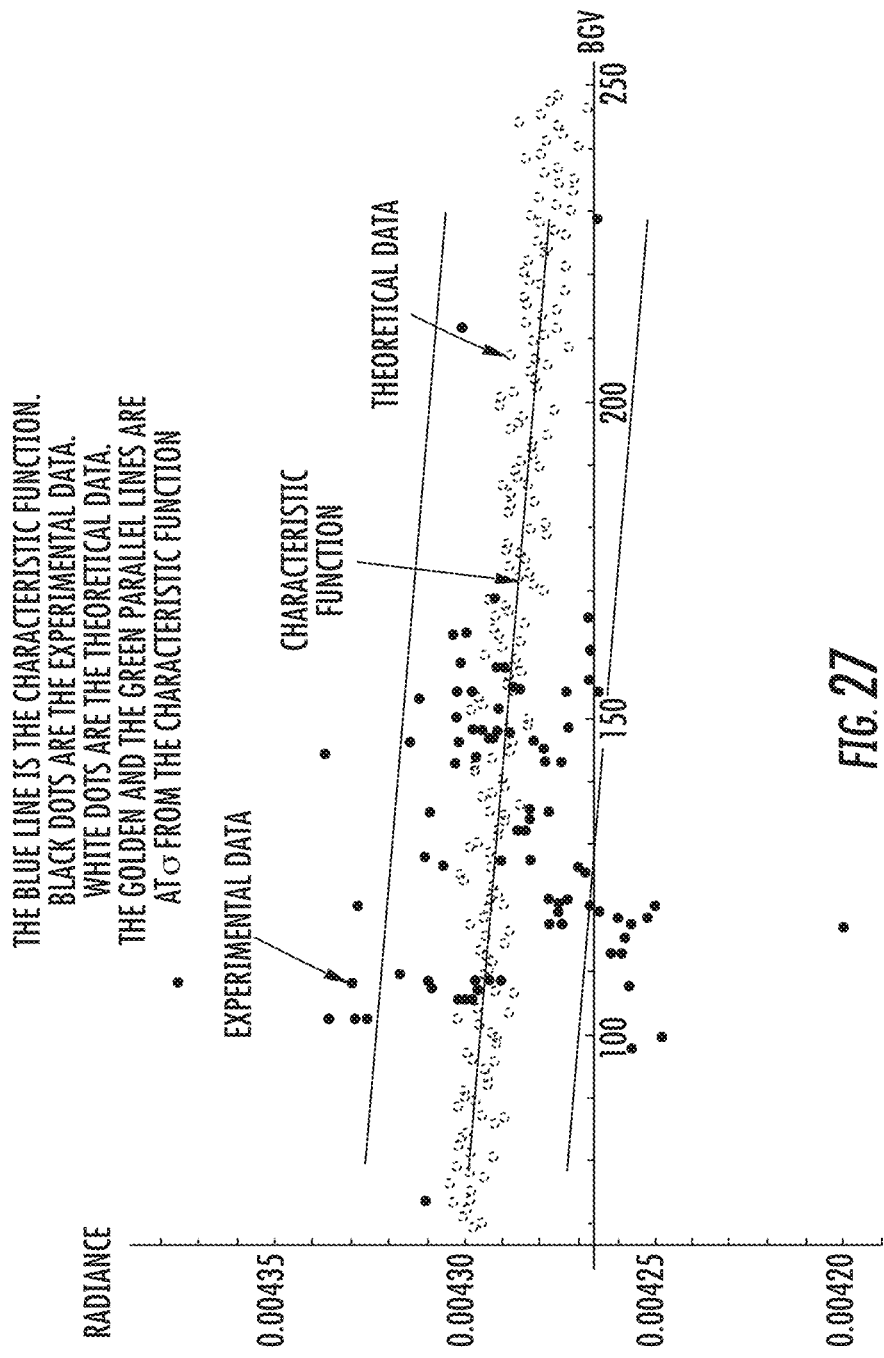
FIG. 27 repeats the plots of FIG. 26 with the number of IR images and hence measurements increased by a factor of 10.

FIG. 27 repeats the plots of FIG. 26 with the number of IR images and hence measurements increased by a factor of 10. These are averaged to form the noise field which is, as expected, narrowed.

Increasing the number of images taken per BGV evaluation improves the measurement accuracy. In an optical glucometer, the data acquisition strategy may include the collection and averaging of about 50 images or more. The time required would be in the seconds' range so a patient would be unaware of the data collection and processing.

There are two types of data that for glucose measurements can be applied for BGV determinations. One is the experimental data, or the historical data, for particular patient. The other is a data set generated by using the EyeModel and statistical variations around it that match the historical data in terms of its range. In the following the search algorithm that can be used to identify the most probable glucose reading will be demonstrated.

The search method is related to what could be called a nearest neighbor search. However, in order to apply this technique, the basic data must be prepared and placed in a data space. The following expression shows how the distance data set is determined. In the first case, the historical data is used.

Historical Data:

This method uses the known BGV and multiplies the associated radiance values by 10000. This has the effect of a units change from radiance in Watts/cm$^2$ to Watts/m$^2$. This creates a two-dimensional space of comparable units and the distance between all of the points can then be determine using the Pythagorean method.

DistHistData==Table[{HistoricalData[[$i$,1]],
10000HistoricalData[[$i$,2]]},{$i$,NumberofDataelements}]

i.e. the DistaHistData is the set BGV and Radiance in Watts/m$^2$ over all data elements.

From this data, a distance matrix can be computed. However, this matrix, is an array of two-dimensional distance matrices. This is because the distances are determined by ranging over the total number of historical data points and then over the range of possible BGV. The following example illustrates the method.

Suppose a patient wants to determine their blood glucose value and uses an infrared sensor (e.g., an optical glucometer system as described herein) and the patient measures a radiance value of 0.004287 radians per square cm. Applying the EyeModel, the predicted BGV is 167.75 mg/dL.

The historical data does not contain this radiance or Rad value, but there are close values in the historical data i.e. {0.00428749, 157.975}, {0.00428761, 128.6}, {0.00428794, 136.1}. These indicate BGV somewhere between 126 and 158. The EyeModel prediction is outside of this range at 168.

The distance matrix is computed using $$DT = \text{Table}\left[\text{Table}\left[\left\{\sqrt{\frac{(10000\,\text{Rad} - \text{DistHistData}[[i, 2]])^2 +}{(P - \text{DistHistData}[[i, 1]])^2}}\right\}, \{P, 30, 230\}\right], \{i, 38\}\right].$$

DT is the array of all distances between all historical data points and all possible points with a radiance of 0.004287 Watts/cm² and all BGV values. In this case, DT is a {38, 201, 1} array. Here "P" is a variable that represents BGV that ranges over all possible integer values from 30 to 230, while "i" ranges over all historical data points, here about 100. The 5 smallest distance values, or those closest to the observed radiance value, 0.004287, are then found and listed:

{0.0254805, 0.045561, 0.0556082, 0.100436, 0.100579}
which correspond to the points:
{{158,0.00428749}, {130,0.00429156}, {154, 0.00429197}, {136.0.00428794}, {105,0.00428592}}.

The best match is a BGV of 158 which is, by design, within the historical data set.

Figure 28:
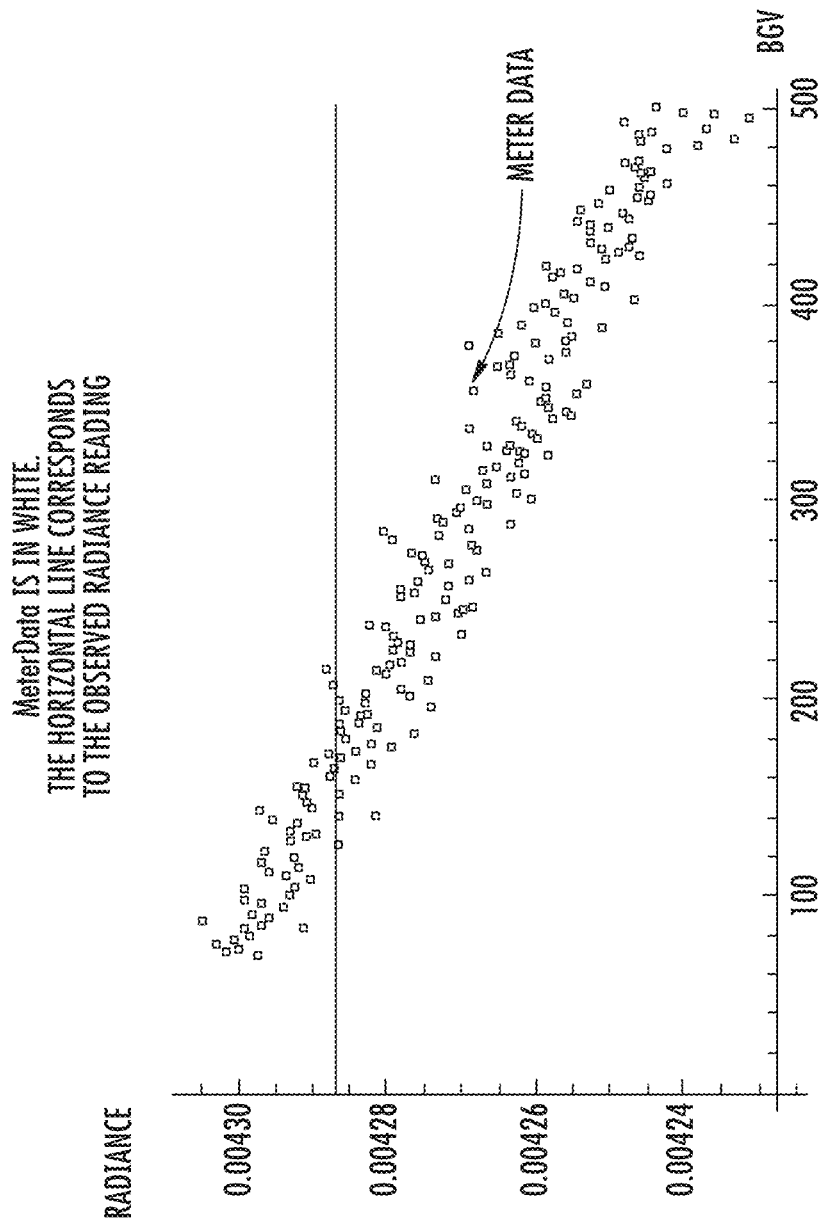
FIG. 28 illustrates a new data set, MeterData, obtained with the EyeModel expression plus randomly generated noise.

Generated Data:

Much greater accuracy can be achieved by increasing the search data set. FIG. 28 illustrates a new data set, MeterData, obtained with the EyeModel expression plus randomly generated noise as described above. This data simulates the average of 40 IR images. The BGV range of 70 to 500 is used in the example.

Again, DT is computed but now using the MeterData and in this case, DT is a {216, 111, 1} array. Here "P" ranges over all possible integer BGVs from 70 to 180 while "'i'" ranges over all 216 MeterData points. The P range is reduced to speed calculations. The 5 smallest DT values (shown by dashed box in FIG. 29) are then found and listed:

{168,0.00428706}, {150,0.00428733}, {124, 0.00428655}, {142,0.00428653}, {136,0.00428753}

Figure 29:
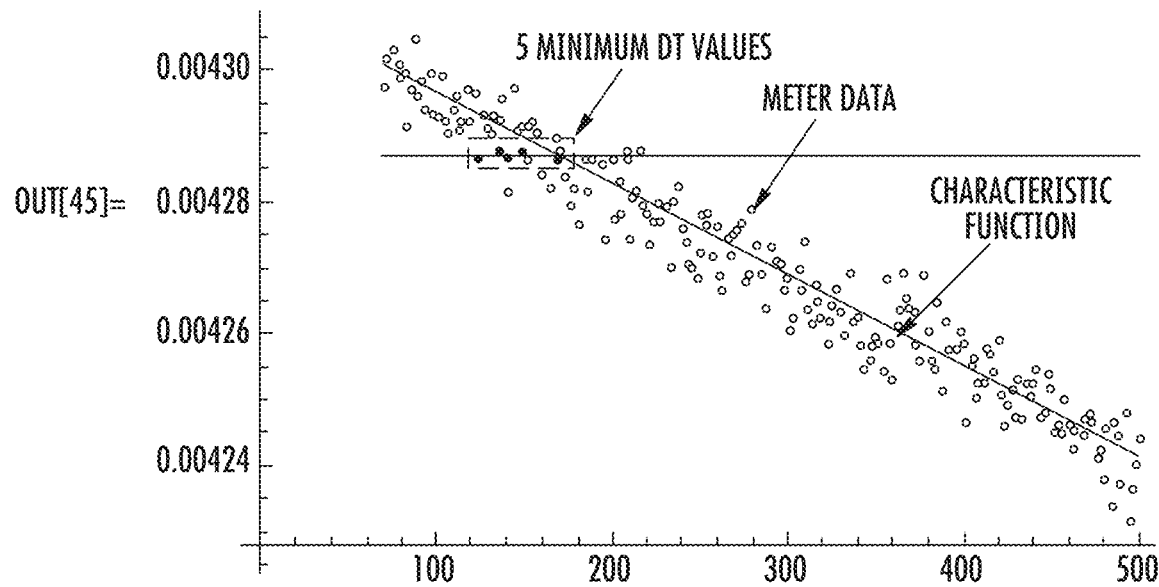
FIG. 29 illustrates the results of the MeterData set obtained by EyeModel plus randomly generated noise with 5 smallest DT values shown in the dashed box.
Figure 30:
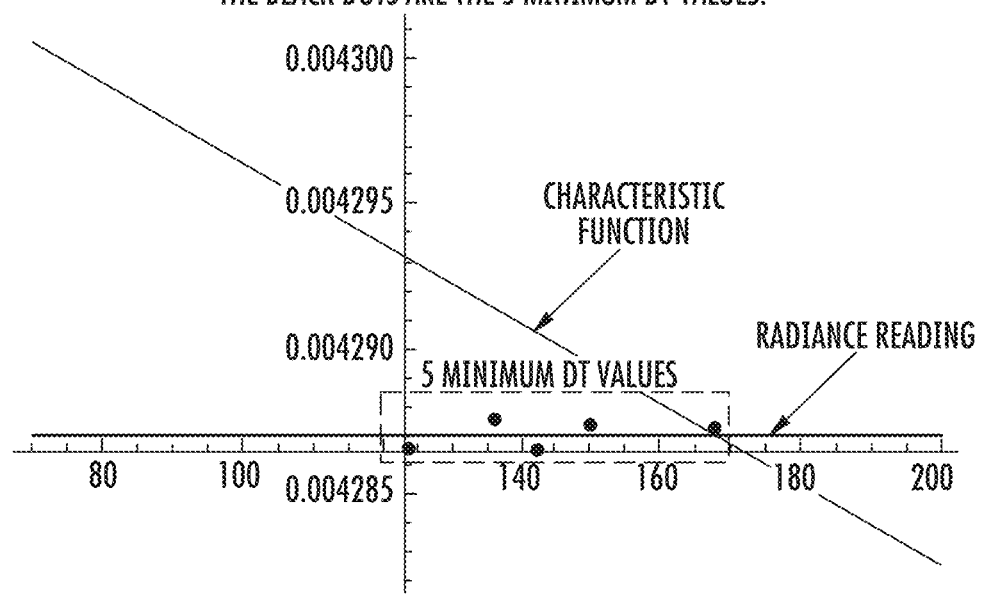
FIG. 30 is a blown up illustration of the 5 smallest DT values shown in FIG. 29.

Now the closet point that matches for the BGV of 168. FIG. 29 illustrates the results of the MeterData set obtained by EyeModel plus randomly generated noise with 5 smallest DT values shown in the dashed box. FIG. 30 is a blown up illustration of the 5 smallest DT values shown in FIG. 29, with the Radiance reading (horizontal line) and EyeModel plot (diagonal line). While 5 DT value points were identified, only one DT value is on the EyeModel plot line at 168.

Another way to interpret these results is that the average of the 5 points is {144, 0.004287} with a standard deviation of {16.4317, 4.53313*10⁻⁷}. BGV is therefore 144+/−16.4. The more probable value would be 144+16.4, 160.4, because this is closer to the EyeModel line.

System Incorporating FLIR LEPTON Camera

Referring now to FIGS. 6B-6D, an example system incorporating a FLIR LEPTON camera is shown. The basic system using the Lepton detectors employs a black body reference, ideally held at a fixed temperature near the average eye temperature, and the Lepton camera plus a computing device. The detector records the reference temperature and makes images of the patient's eye. As shown in FIG. 6B, the system is configured to take images of the patient's eye 651. The system includes an ocular tube having a moveable portion 652 and fixed portion 653. Additionally, the system includes a thermal reference 654 (i.e., black body (BB)) and an IR camera (i.e., FLIR LEPTON camera) 655. The system further includes a shutter 656. The shutter 656 is a movable assembly that allows the IR camera 655 to observe the BB reference 654. It consists of an upper part (see FIG. 6C) that is the normal optical path between the eye 651 and the IR camera 655. The lower part (see FIG. 6D) changes the optical path such that radiation front the BB reference 654 goes directly to the IR camera 655. The shutter 656 provides a means of obtaining the eye temperature over the field of view. This can be accomplished by heating or cooling the BB reference 654 until the ratio of EYE/BB value is one. This can improve the accuracy of the measurements.

Figure 32:
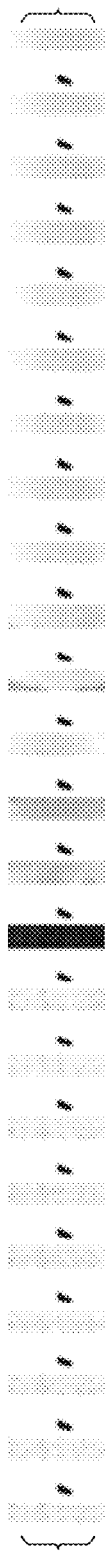
FIG. 32 illustrates a series of 24 images captured using the apparatus described with respect to FIGS. 6B-6D.

Referring now to FIG. 31, images of a black body reference and patient's eye captured using a system described with respect to FIGS. 6B-6D are shown. FIG. 31 also illustrates the mask used to isolate a portion of the patient eye. The IR camera makes a series of 24 or more images (e.g., 80×40 pixel images) within a 6 second period that includes a black body reference and the patient's eyes. The number of pixels used for the radiation detection in the eye is about 100, while for the black body 480 pixels are used. FIG. 32 illustrates a series of 24 images captured as described above.

In this example, the first 6 images are of the BB and when reduced to grey scale (GS) pixel values yields and average of 0.9202 per pixel, the BB value. The last 9 images are of the eye center and has a gray scale (GS) pixel average of 0.8963, the EYE value. When coupled with the BB temperature one obtains a data set such as:

{BB,EYE,Temperature}→{0.920156,0.896342,30.7}.

One example of typical data is of the form:
{0.8844190268700072', 0.8598140885984022', 31.4' } which corresponds to a BGV of 134 mg/dL. The BB and EYE readings are in average grey scale pixel values.

This data is then processed in terms of EYE/BB ratios and compared with the BGV.

Figure 33:
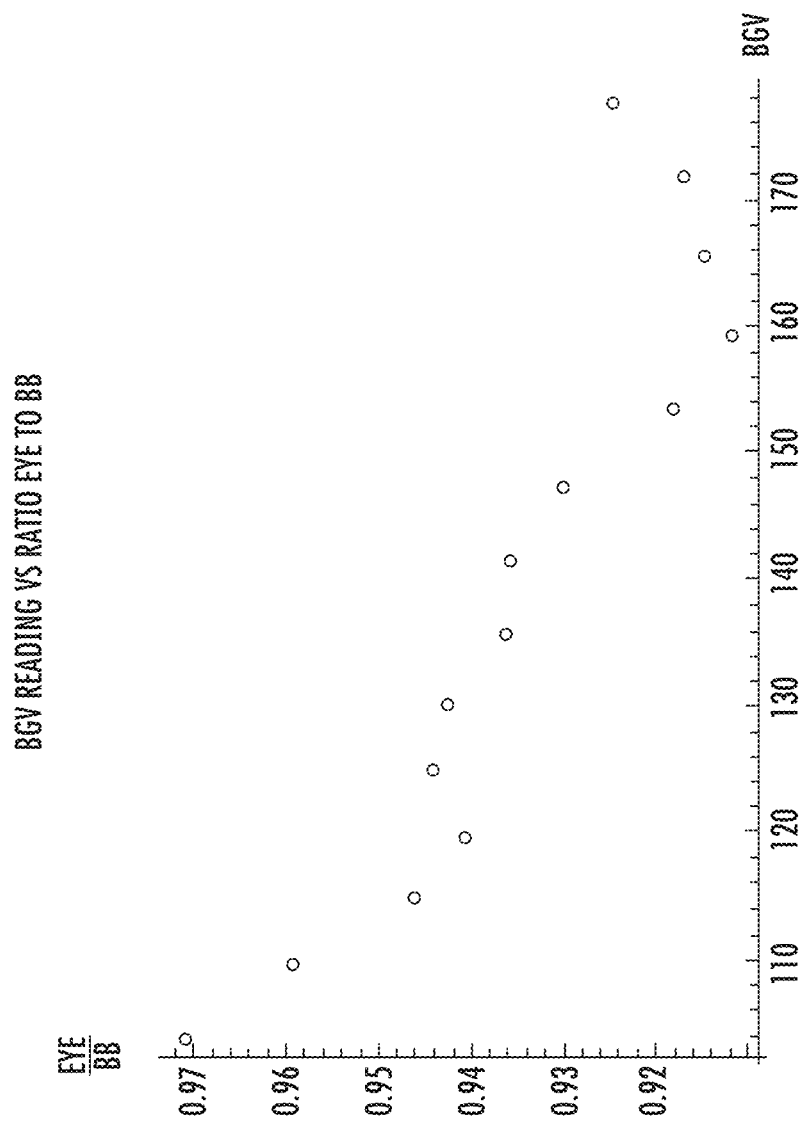
FIG. 33 illustrates a plot that shows the expected trend, i.e. that radiance decreases with increasing BGVs.
Figure 34:
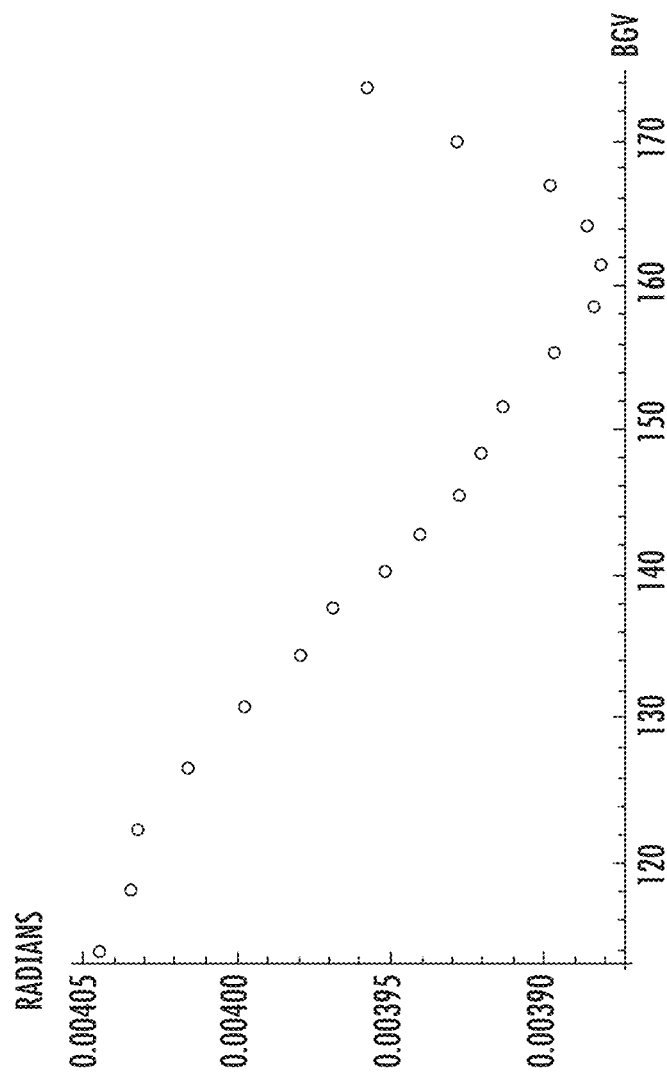
FIG. 34 illustrates a plot of eye to black body (BB) radiance reference ratio versus BGV.
Figure 35:
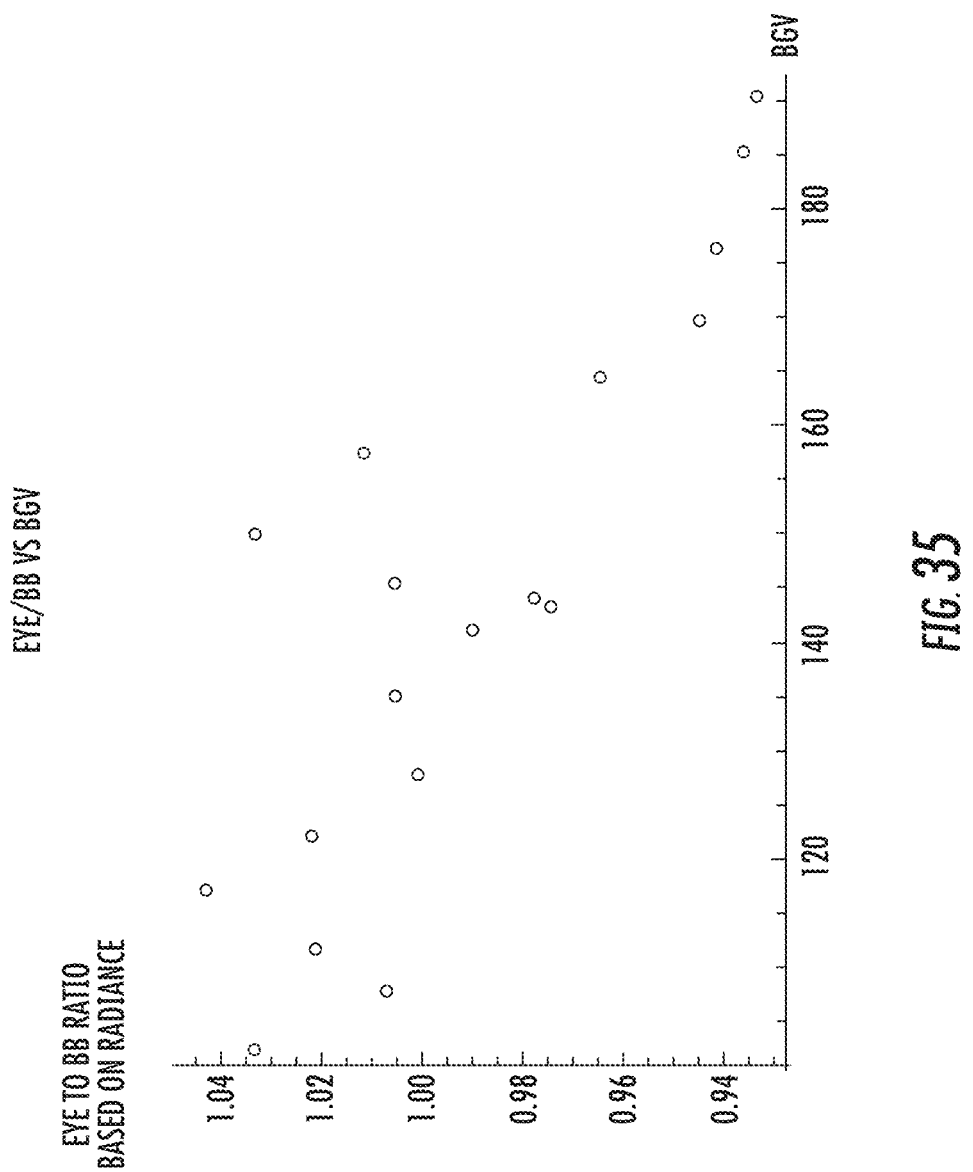
FIG. 35 illustrates a plot of eye to black body (BB) radiance reference ratio versus BGV.

FIGS. 33-35 illustrate plots, smoothed using a moving average algorithm, represent the results. The data set used here includes 29 independent points.

FIG. 33 illustrates a plot that shows the expected trend, i.e. that radiance decreases with increasing BGVs. Since all of the previous work has been in terms of radians, the data shown in FIG. 33 has also been converted Radians versus BGV.

FIGS. 34 and 35 illustrate plots of eye to black body (BB) radiance reference ratio. The plots are not identical in general form because the conversion uses a black body function to determine radians per gray scale unit (GSU) pixels which is temperature dependent.

Both the plots in FIGS. 34 and 35 show a "turn up" for BGV above 160 mg/dL. This appears to be noise in the data and should not be present when more data is included. In particular, for the diabetic test subject studied here BGV above 160 are rare, hence the higher values here do not have the benefit of a larger population average.

This effect is reduced when the radiance ratios are considered as shown in the following FIG. 35. This data has been smoothed with a moving average algorithm. There is a strong correlation between this ratio and BGV.

Even though the FLIR LEPTON camera includes a VOX sensor, it is more susceptible to signal drifting than a system including more complex camera (e.g., FLIR A325sc camera). One way to address signal drift is to use the ratio of EYE/BB which is invariant with respect to signal drifting but not to eye radiance variations. Continuous monitoring of a black body standard would facilitate a reasonably accurate diagnostic measurement.

FIGS. 36A-36D illustrate an example handheld optical glucometer used to collect the data shown in FIGS. 33-35. The handheld optical glucometer includes a device body 670 in which an IR camera 675 (i.e., FLIR LEPTON camera) is mounted. The device body 670 is designed to maintain the eye at a fixed and stable distance from the IR camera 675. This design also fits into the eye socket so that the eye will always be centered in the IR camera 675 field of view. The eye is about 4 cm from the IR camera 675 so there is no contact. One does not need to apply high pressure to hold the device in place, so there is no discomfort to the patient. As described herein, the IR camera 675 interfaces with a computing device (e.g., computing device 600 of FIG. 6E) for image processing and analyses. This disclosure contemplates that the computing device can be part of, or external to, the handheld optical glucometer.

Those skilled in the art will recognize, or be able to ascertain using no more than routine experimentation, many equivalents to the specific embodiments of the invention described herein. Such equivalents are intended to be encompassed by the following claims.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. An apparatus for detecting blood glucose levels in a subject, comprising:
   a thermographic imaging device configured to capture mid-infrared (MIR) electromagnetic emissions; and
   a computing device communicatively connected to the thermographic imaging device, wherein the computing device comprises a processor and memory operably connected to the processor, wherein the memory has computer-executable instructions stored thereon that, when executed by the processor, cause the processor to:
   receive a plurality of images of the subject's eye captured by the thermographic imaging device;
   using the plurality images of the subject's eye, calculate an average radiance value for a pixel region of interest;
   correct the average radiance value for the pixel region of interest based on a temperature of the subject's eye at the time of image capture; and
   correlate the corrected average radiance value for the pixel region of interest to a blood glucose value of the subject.

2. The apparatus of claim 1, wherein the plurality of images is four images.

3. The apparatus of claim 1, wherein the MIR electromagnetic emissions are in a wavelength range from about 9 µm to about 11 µm.

4. The apparatus of claim 3, wherein the MIR electromagnetic emissions are in a wavelength range from about 9.7 µm to about 10.3 µm.

5. The apparatus of claim 1, wherein calculating the average radiance value for the pixel region of interest comprises calculating a respective average radiance value in the pixel region of interest for each of the plurality of images, and wherein the average radiance value for the pixel region of interest is an average value of the respective average radiance values.

6. The apparatus of claim 1, wherein the thermographic imaging device is an infrared camera.

7. The apparatus of claim 1, wherein the thermographic imaging device is a microbolometer.

8. The apparatus of claim 7, wherein the microbolometer is a vanadium oxide (VOX) or amorphous silicon (a-Si) microbolometer.

9. The apparatus of claim 7, wherein the microbolometer comprises a focal plane array of about 100×100 active pixels.

10. The apparatus of claim 1, wherein correcting the average radiance value for the pixel region of interest based on the temperature of the subject's eye at the time of image capture comprises scaling the average radiance value for the pixel region of interest to a corresponding radiance value at about 33.5° C.

11. The apparatus of claim 1, wherein correlating the corrected average radiance value for the pixel region of interest to the blood glucose value of the subject comprises querying a database to obtain the blood glucose value of the subject corresponding to the corrected average radiance value for the pixel region of interest.

12. The apparatus of claim 11, wherein correlating the corrected average radiance value for the pixel region of interest to the blood glucose value of the subject further comprises using a search algorithm to identify a most probable blood glucose value of the subject corresponding to the corrected average radiance value for the pixel region of interest.

13. The apparatus of claim 1, further comprising:
   a frame configured to align a sensor of the thermographic imaging device in front of the subject's eye; and
   a collimating ring limiting a field of view of the sensor to a defined region about the center of the subject's eye, wherein the collimating ring defines the distance from the detector to the subject's eye.

14. The apparatus of claim 1, wherein the apparatus is incorporated into a handheld electronic device.

15. A method for detecting blood glucose levels in a subject, comprising:
   capturing, using a thermographic imaging device, a plurality of images of the subject's eye;
   calculating, using a computing device, an average radiance value for a pixel region of interest based on the plurality images of the subject's eye;
   correcting, using the computing device, the average radiance value for the pixel region of interest based on a temperature of the subject's eye at the time of image capture; and
   correlating, using the computing device, the corrected average radiance value for the pixel region of interest to a blood glucose value of the subject.

16. The method of claim 15, further comprising transmitting the plurality of images of the subject's eye to the computing device over a communication link.

17. The method of claim 15, wherein calculating the average radiance value for the pixel region of interest comprises calculating a respective average radiance value in the pixel region of interest for each of the plurality of images, and wherein the average radiance value for the pixel region of interest is an average value of the respective average radiance values.

18. The method of claim 15, wherein correcting the average radiance value for the pixel region of interest based on the temperature of the subject's eye at the time of image capture comprises scaling the average radiance value for the pixel region of interest to a corresponding radiance value at about 33.5° C.

19. The method of claim 15, further comprising assaying a blood sample from the subject to measure blood glucose level if an abnormal glucose value is returned in response the correlation step.

20. The method of claim 15, further comprising adjusting glucose level in the subject based on the glucose value returned in response the correlation step.

21. A blood-glucose detection apparatus comprising:
a mid-infrared (MIR) electromagnetic emissions sensor having a plurality of pixels configured to receive a field of view,
a frame configured to align the sensor in front of a subject's eye,
a collimating ring limiting the field of view to a defined region about the center of the eye, wherein the collimating ring defines the distance from the detector to the subject's eye,
a processor and computerized memory configured to measure blood glucose concentration in the subject by initiating computer implemented instructions to:
store a set of standard control values comprising average control radiance values, for a selected wavenumber, induced at the pixels for MIR emitted through respective transmission media having known glucose concentrations, wherein the control values are accessible by the processor,
receive, in a measurement cycle utilizing the selected wavenumber, a radiance measurement corresponding to MIR incident upon each of the respective pixels;
calculate an average radiance measurement from the respective radiance measurements corresponding to respective measurement cycles in a plurality of measurement cycles;
correlate the average radiance measurement to the known glucose concentration having a control radiance value equal to the average radiance measurement.

22. An optical glucometer comprising:
an infrared camera comprising an array of pixels connected to a processor that correlates blood glucose values to radiance measurements induced by mid-infrared radiation (MIR) incident upon the respective pixels; and
computer memory connected to the processor, the computer memory storing a set of standard control values comprising average control radiance values, for a selected wavenumber, induced at the pixels for MIR emitted through respective transmission media having known glucose concentrations, wherein the control values are accessible by the processor, and
the processor is configured to:
receive, in a measurement cycle utilizing the selected wavenumber, a radiance measurement corresponding to MIR incident upon each of the respective pixels;
calculate an average radiance measurement from the respective radiance measurements corresponding to respective measurement cycles in a plurality of measurement cycles;
correlate the average radiance measurement to the known glucose concentration having a control radiance value equal to the average radiance measurement.

23. The optical glucometer according to claim 22, wherein the array of pixels is configured to transmit a thermal image of an eye to the processor, and the processor is configured to convert the thermal image to a grayscale image of radiance values.

24. The optical glucometer according to claim 23, wherein the processor is configured to receive the radiance measurements for a subset of pixels corresponding to a localized section of an image of eye and multiply the respective radiance measurements for each pixel by a corresponding grayscale image value prior to calculating the average.

25. The optical glucometer according to claim 24, wherein radiance values at the pixels are normalized to reference values calculated as reference radiance values induced at pixels by a black body reference emission of MIR.

26. A method of measuring blood glucose concentration in eye, comprising:
storing a set of standard control values, wherein the set of standard control values comprises average control radiance values, for a selected wavenumber, induced at pixels of a mid-infrared radiation (MIR) sensor for MIR emitted through respective transmission media having known glucose concentrations;
storing, during a measurement cycle, radiance measurements corresponding to mid-infrared radiation (MIR) emitted from the eye and incident upon the pixels;
calculating an average radiance measurement from the respective radiance measurements corresponding to respective measurement cycles in a plurality of measurement cycles; and
correlating the average radiance measurement to the known blood glucose concentration having an average control radiance value equal to the average radiance measurement.

27. The method according to claim 26, wherein the wavenumber is 1030 cm$^{-1}$ or 1078 cm$^{-1}$.

28. The method according to claim 26, further comprising extracting from a thermal image of the pixels the average radiance measurement and a temperature value for a localized area of the pixels.

* * * * *